US011135080B2

(12) United States Patent
Lee et al.

(10) Patent No.: US 11,135,080 B2
(45) Date of Patent: Oct. 5, 2021

(54) FRAME ASSEMBLY AND MOTION ASSISTANCE APPARATUS INCLUDING THE SAME

(71) Applicants: Samsung Electronics Co., Ltd., Suwon-si (KR); Korea University of Technology and Education Industry University Cooperation Foundation, Cheonan-si (KR)

(72) Inventors: Youn Baek Lee, Yongin-si (KR); Yong-Jae Kim, Cheonan-si (KR)

(73) Assignees: Samsung Electronics Co., Ltd., Gyeonggi-do (KR); Korea University of Technology and Education Industry-University Cooperation Foundation, Cheonan-Si (KR)

( * ) Notice: Subject to any disclaimer, the term of this patent is extended or adjusted under 35 U.S.C. 154(b) by 1041 days.

(21) Appl. No.: 15/358,557

(22) Filed: Nov. 22, 2016

(65) Prior Publication Data

US 2017/0151083 A1 Jun. 1, 2017

(30) Foreign Application Priority Data

Nov. 26, 2015 (KR) .................. 10-2015-0166069
Aug. 22, 2016 (KR) .................. 10-2016-0106039

(51) Int. Cl.
*A61F 5/01* (2006.01)
*A61H 1/02* (2006.01)
*A61H 3/00* (2006.01)

(52) U.S. Cl.
CPC .......... *A61F 5/0125* (2013.01); *A61F 5/0104* (2013.01); *A61F 5/0106* (2013.01);
(Continued)

(58) Field of Classification Search
CPC ...... A61F 5/0123; A61F 5/0127; A61F 5/013; A61F 5/0125; A61F 2005/0155;
(Continued)

(56) References Cited

U.S. PATENT DOCUMENTS 3,827,431 A * 8/1974 Pecorella ............. A61F 5/0125
602/16
4,856,500 A * 8/1989 Spademan ............ A61F 5/0125
602/26

(Continued)

FOREIGN PATENT DOCUMENTS

CN 104224492 A 12/2014
EP 1 728 492 A1 12/2006

(Continued)

OTHER PUBLICATIONS

Extended European Search Report issued by the European Patent Office dated Mar. 31, 2017 for corresponding EP Patent Application No. 16197533.9.

(Continued)

*Primary Examiner* — Seema Mathew
(74) *Attorney, Agent, or Firm* — Harness, Dickey & Pierce, P.L.C.

(57) ABSTRACT

A frame assembly includes a first longitudinal member, a second longitudinal member spaced apart from the first longitudinal member, and a plurality of distance maintaining members connected between the first longitudinal member and the second longitudinal member, and configured to maintain a distance between the first longitudinal member and the second longitudinal member.

18 Claims, 32 Drawing Sheets

(52) U.S. Cl.
CPC ............ *A61F 5/0123* (2013.01); *A61H 1/024* (2013.01); *A61H 1/0266* (2013.01); *A61F 2005/0146* (2013.01); *A61F 2005/0167* (2013.01); *A61H 3/00* (2013.01); *A61H 2201/0192* (2013.01); *A61H 2201/12* (2013.01); *A61H 2201/165* (2013.01)

(58) Field of Classification Search
CPC ........ A61F 2005/0151; A61F 2005/016; A61F 2005/0146; A61F 2005/0144; A61F 25/0125; A61H 1/024
See application file for complete search history.

(56) References Cited

U.S. PATENT DOCUMENTS

| | | | |
|---|---|---|---|
| 5,000,169 A * | 3/1991 | Swicegood | A61F 5/0125 128/882 |
| 5,013,037 A * | 5/1991 | Stermer | A63B 21/023 482/122 |
| 5,092,321 A * | 3/1992 | Spademan | A61F 5/0585 602/16 |
| 5,178,137 A * | 1/1993 | Goor | A61F 5/0111 601/40 |
| 5,980,435 A * | 11/1999 | Joutras | A43B 1/0054 482/114 |
| 6,024,713 A * | 2/2000 | Barney | A61F 5/0125 602/16 |
| 6,524,265 B2 * | 2/2003 | Hogg | A61F 5/0102 602/16 |
| 7,097,627 B2 * | 8/2006 | Enzerink | A61F 5/0125 602/23 |
| 8,037,546 B2 * | 10/2011 | Jewell | A41D 13/0581 2/227 |
| 8,419,670 B2 * | 4/2013 | Downing | A61F 5/0123 602/26 |
| 8,771,210 B2 | 7/2014 | Smith et al. | |
| 8,945,032 B2 * | 2/2015 | Nevels | A61F 5/373 602/19 |
| 9,770,356 B2 * | 9/2017 | Ingimundarson | A61F 5/0123 |
| 10,413,437 B2 * | 9/2019 | Romo | A61F 5/0123 |
| 10,434,002 B2 * | 10/2019 | Merkley | A61F 5/01 |
| 10,744,022 B2 * | 8/2020 | Lee | A61F 2/60 |
| 10,898,363 B2 * | 1/2021 | Ingimundarson | A61F 5/0123 |
| 2003/0135144 A1 * | 7/2003 | Hogg | A61F 5/0125 602/23 |
| 2006/0100560 A1 * | 5/2006 | Gilmour | A61F 5/0123 602/26 |
| 2013/0296746 A1 * | 11/2013 | Herr | A61H 3/00 601/34 |
| 2016/0015589 A1 | 1/2016 | Lee et al. | |
| 2016/0030271 A1 | 2/2016 | Roh et al. | |
| 2016/0038328 A1 | 2/2016 | Choi et al. | |
| 2016/0038368 A1 | 2/2016 | Lee et al. | |
| 2016/0045387 A1 | 2/2016 | Lee et al. | |
| 2016/0081870 A1 | 3/2016 | Lee et al. | |
| 2016/0106615 A1 | 4/2016 | Lee et al. | |
| 2016/0193102 A1 | 7/2016 | Roh et al. | |
| 2017/0027735 A1 * | 2/2017 | Walsh | A61F 5/0102 |
| 2019/0070062 A1 * | 3/2019 | O'Donnell | A61F 5/01 |

FOREIGN PATENT DOCUMENTS

| | | |
|---|---|---|
| JP | 2004344306 A | 12/2004 |
| JP | 2005-059110 A | 3/2005 |
| JP | 2010017535 A | 1/2010 |
| JP | 2010075548 A | 4/2010 |
| JP | 2014-172116 A | 9/2014 |
| JP | 2015-123563 A | 7/2015 |
| KR | 100481642 B1 | 4/2005 |
| KR | 200382803 Y1 | 4/2005 |
| KR | 20160009869 A | 1/2016 |
| WO | WO-2014/109799 A1 | 7/2014 |
| WO | WO-2015/157731 A1 | 10/2015 |

OTHER PUBLICATIONS

Chinese Office Action dated Dec. 24, 2019 for Chinese Patent Application No. 201611071197.3.

Japanese Office Action issued by the Japanese Patent Office dated Aug. 3, 2021 for corresponding JP Patent Application No. 2016-224009.

* cited by examiner

<u>19</u>

FRAME ASSEMBLY AND MOTION ASSISTANCE APPARATUS INCLUDING THE SAME

CROSS-REFERENCE TO RELATED APPLICATIONS

This application claims under 35 U.S.C. § 119 to Korean Patent Application No. 10-2015-0166069 filed on Nov. 26, 2015 and Korean Patent Application No. 10-2016-0106039 filed on Aug. 22, 2016 in the Korean Intellectual Property Office, the entire contents both of which are incorporated herein by reference in their entirety.

BACKGROUND

Field

At least one example embodiment relates to a frame assembly and/or a motion assistance apparatus including the same.

Description of the Related Art

Motion assistance apparatuses enabling the elderly and/or patients having joint problems to walk with less effort, and motion assistance apparatuses increasing muscular strength of human bodies for military purposes have been developed.

SUMMARY

Some example embodiments relate to a frame assembly.

In some example embodiments, the frame assembly includes a first longitudinal member; a second longitudinal member spaced apart from the first longitudinal member; and a plurality of distance maintaining members connecting the first longitudinal member and the second longitudinal member, the plurality of distance maintaining members configured to maintain a distance between the first longitudinal member and the second longitudinal member.

In some example embodiments, the first longitudinal member and the second longitudinal member each have ends with an intermediate portion therebetween, and the plurality of distance maintaining members connect the first longitudinal member and the second longitudinal member such that the intermediate portion of the second longitudinal member moves relative to the intermediate portion of the first longitudinal member.

In some example embodiments the second longitudinal member is parallel with the first longitudinal member.

In some example embodiments the frame assembly has ends with an intermediate portion therebetween, and the intermediate portion of the frame assembly is configured to flex in response to a force applied in a lateral direction thereto.

In some example embodiments the first longitudinal member and the second longitudinal member each include a flexible material.

In some example embodiments, a length of each of the plurality of distance maintaining members is less than a length of each of the first longitudinal member and the second longitudinal member.

In some example embodiments, adjacent ones of the plurality of distance maintaining members are separated by a distance, the distance being less than a length of each of the plurality of distance maintaining members.

In some example embodiments, the plurality of distance maintaining members each include a first material, the first longitudinal member includes a second material and the second longitudinal member includes a third material, the first material being stiffer than the second material and the third material.

In some example embodiments, at least one of the plurality of distance maintaining members has a first end portion and a second end portion with an intermediate portion therebetween, and the first end portion and the second end portion of the at least one of the plurality of distance maintaining members are fixed to the first longitudinal member and the second longitudinal member, respectively.

In some example embodiments, both of the first end portion and the second end portion of the at least one of the plurality of distance maintaining members are more flexible than the intermediate portion of the at least one of the plurality of distance maintaining members.

In some example embodiments, at least one of the first end portion and the second end portion of the at least one of the plurality of distance maintaining members is rotatably fixed to one of the first longitudinal direction and the second longitudinal member.

In some example embodiments, at least one of the plurality of distance maintaining members includes a first slider and a second slider, a first one of the first slider and the second slider being configured to slide relative to a second one of the first slider and the second slider.

In some example embodiments, the at least one of the plurality of distance maintaining members further includes a separation preventing member configured to inhibit separation between the first slider and the second slider.

In some example embodiments, at least one of the plurality of distance maintaining members is slidably connected to one of the first longitudinal member and the second longitudinal member.

In some example embodiments, the first longitudinal member and the second longitudinal member each have a first end and a second end with an intermediate portion therebetween, and the frame assembly further includes a first object and a second object, the first object connected to the first end of the first longitudinal member and the first end of the second longitudinal member, and the second object connected to the second end of the first longitudinal member and the second end of the second longitudinal member.

In some example embodiments, the second end of the second longitudinal member is connected to the second object such that the second end of the second longitudinal member moves in a direction that intersects a longitudinal direction of the second object.

In some example embodiments, at least one of the plurality of distance maintaining members has a first end portion and a second end portion with an intermediate portion therebetween, and the first end portion of at least one of the plurality of distance maintaining members is fixed to the first longitudinal member, and the second end portion of the at least one of the plurality of distance maintaining members is slidably connected to the second longitudinal member.

In some example embodiments, the first object is configured to support a first portion of a user, and the second object is configured to support a second portion of the user, the first portion and the second portion of the user being on opposite sides of a joint of the user.

In some example embodiments, the frame assembly is configured to apply a torque to the second object to rotate the second object relative to the first object, if a tensile force is applied to the second longitudinal member.

In some example embodiments, the first longitudinal member is on a first side of the first portion and the second portion of the user, and the second longitudinal member is on the first side of the first portion and the second portion of the user, and the frame assembly further includes: a third longitudinal member on a second side of the first portion and the second portion of the user such that the third longitudinal member is opposite the first longitudinal member, the third longitudinal member configured to connect the first object and the second object; a fourth longitudinal member on the second side of the first portion and the second portion of the user such that the fourth longitudinal member is opposite the second longitudinal member, the fourth longitudinal member configured to connect the first object and the second object; and a plurality of second distance maintaining members fixed to the third longitudinal member, the plurality of second distance maintaining members slidably connected to the fourth longitudinal member.

In some example embodiments, the first longitudinal member is an elastic body.

In some example embodiments, a height of at least one of the plurality of distance maintaining members decreases from the first longitudinal member toward the second longitudinal member.

Some example embodiments relate to a motion assistance apparatus.

In some example embodiments, the motion assistance apparatus includes a first object configured to attach to a first portion of a user; a second object configured to attach to a second portion of the user; and a frame assembly including, a first longitudinal member configured to connect the first object and the second object, a second longitudinal member spaced apart from the first longitudinal member, and a plurality of distance maintaining members connecting the first longitudinal member and the second longitudinal member.

In some example embodiments, the motion assistance apparatus further includes a rotary body connected to one of the first longitudinal member and the second longitudinal member, wherein the frame assembly is configured to perform one of a flexion motion and an extension motion based on a direction of rotation of the rotary body.

In some example embodiments, one of the first longitudinal member and the second longitudinal member is an elastic body, and an initial state of the frame assembly is a flexion state.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
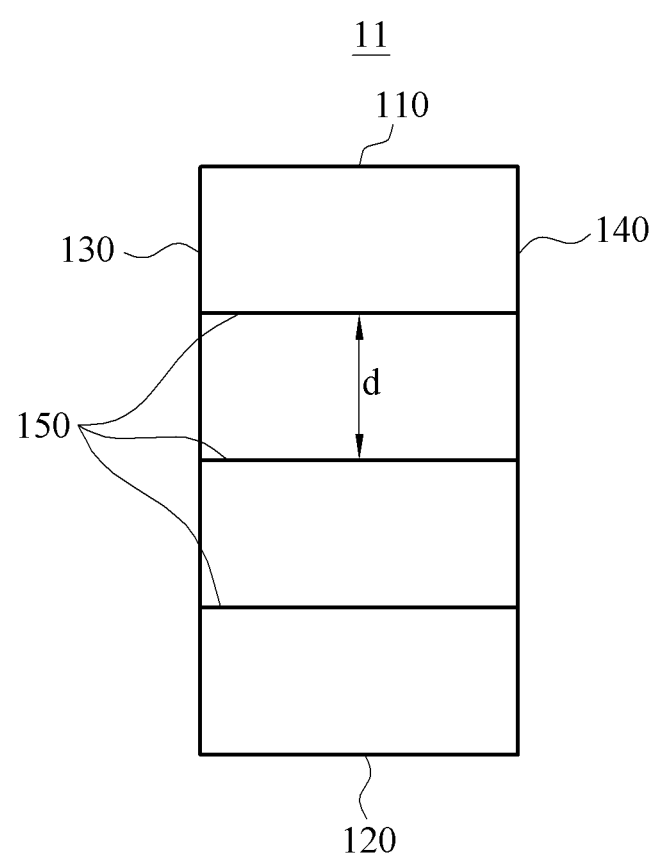
FIG. 1 illustrates a frame assembly according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 illustrates a frame assembly according to at least one example embodiment.

Referring to FIG. 1, a frame assembly 11 may include a first longitudinal member 130, a second longitudinal member 140, and a plurality of distance maintaining members 150. The distance maintaining members 150 may be connected between the first longitudinal member 130 and the second longitudinal member 140. The distance maintaining members 150 may maintain a desired (or, alternatively, a predetermined) distance between the first longitudinal member 130 and the second longitudinal member 140. The distance maintaining members 150 may enable the second longitudinal member 140 to maintain substantially the same distance from the first longitudinal member 130 although the frame assembly 11 is deformed by an external force applied to the frame assembly 11. An intermediate area of one of the first longitudinal member 130 and the second longitudinal member 140 may move relative to an intermediate area of the other of the first longitudinal member 130 and the second longitudinal member 140. The distance maintaining members 150 may enable the frame assembly 11 to maintain a desired (or, alternatively, a predetermined) shape based on bending levels of the two longitudinal members 130 and 140. The distance maintaining members 150 may prevent buckling of the first longitudinal member 130 and the second longitudinal member 140.

The first longitudinal member 130 and the second longitudinal member 140 may each connect a first object 110 and a second object 120. The second longitudinal member 140 may be spaced apart from the first longitudinal member 130, for example, parallel with the first longitudinal member 130. The first longitudinal member 130 and the second longitudinal member 140 may each include a flexible material. One or both of the first longitudinal member 130 and the second longitudinal member 140 may each include a material that is flexible while having a stiffness sufficient to prevent buckling by a self-weight, for example, a material such as synthetic resin. A flexural stiffness of the first longitudinal member 130 and/or the second longitudinal member 140 may be 10% less than a longitude stiffness of the first longitudinal member 130 and/or the second longitudinal member 140. The first longitudinal member 130 and/or the second longitudinal member 140 may be an elastic body that restores the original shape when an external force is not applied thereto.

Both end portions of the first longitudinal member 130 may be fixed to the first object 110 and the second object 120, respectively. Both end portions of the second longitudinal member 140 may also be fixed to the first object 110 and the second object 120, respectively. For example, the first longitudinal member 130 and the second longitudinal member 140 may be provided in a form of plates having sides facing each other.

The distance maintaining members 150 may rotate, bend, or slide relative to the first longitudinal member 130 and/or the second longitudinal member 140. In the above structure, the second longitudinal member 140 may maintain substantially the same distance from the first longitudinal member 130 while the intermediate area of the first longitudinal member 130 and the intermediate area of the second longitudinal member 140 may move relative to sides facing each other. Thus, the frame assembly 11 may have a flexibility in a direction perpendicular to an intermediate area thereof.

Lengths of the distance maintaining members 150 may be less than a length of the first longitudinal member 130 and a length of the second longitudinal member 140. To improve a flexural rigidity of the frame assembly 11, a distance d between two adjacent distance maintaining members 150 in an initial state in which an external force is not applied may be less than the lengths of the distance maintaining members 150. The plurality of distance maintaining members 150 may each include a material that is stiffer than a material included in the first longitudinal member 130 and a material included in the second longitudinal member 140.

Figure 2:
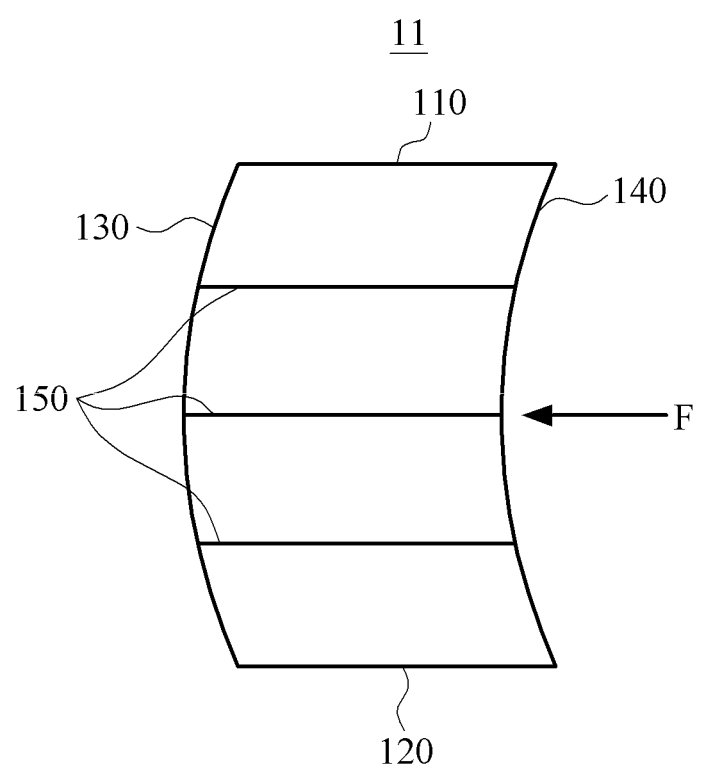
FIG. 2 illustrates an operation of a frame assembly when a force is applied to an intermediate area of the frame assembly in a lateral direction according to at least one example embodiment.

FIG. 2 illustrates an operation of a frame assembly when a force is applied to an intermediate area of the frame assembly in a lateral direction according to at least one example embodiment. FIG. 2 illustrates a case in which the first object 110 and the second object 120 are fixed not to move relative to each other.

Referring to FIG. 2, when a force F is applied to an intermediate area of the frame assembly 11 in a lateral direction, the first longitudinal member 130 and the second longitudinal member 140 may bend by the force F. In this example, the first longitudinal member 130 and the second longitudinal member 140 may move relative to each other while maintaining a distance therebetween through the distance maintaining members 150. For example, in a case in which both end portions of the first longitudinal member 130 are fixed to the first object 110 and the second object 120, respectively, and both ends portions of the second longitudinal member 140 are fixed to the first object 110 and the second object 120, respectively, a relative angle between the first object 110 and the second object 120 may be maintained the same. Thus, the first longitudinal member 130 and the second longitudinal member 140 may bend in the same shapes.

Figure 3:
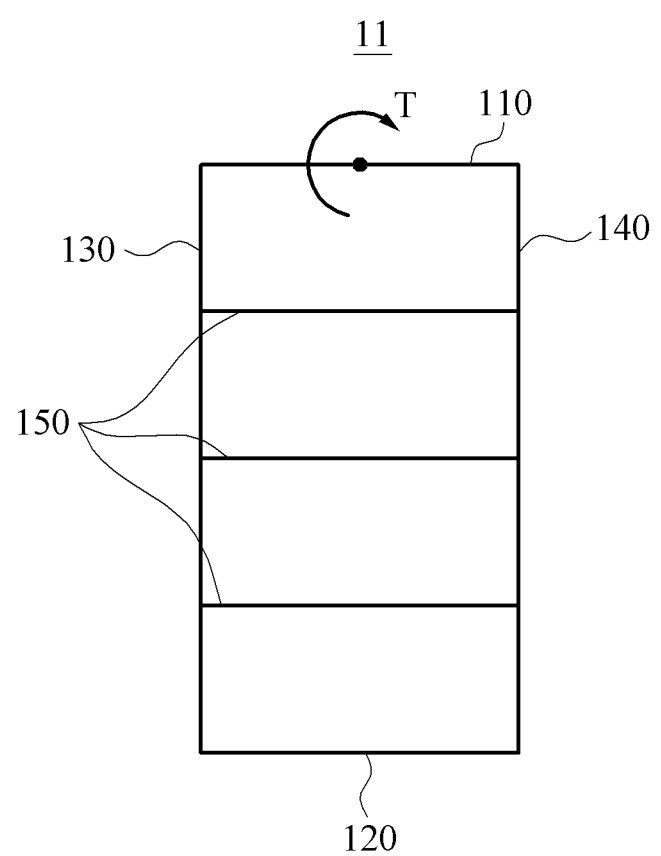
FIG. 3 illustrates an operation of a frame assembly when a torque is applied to an end portion of the frame assembly according to at least one example embodiment.
Figure 4:
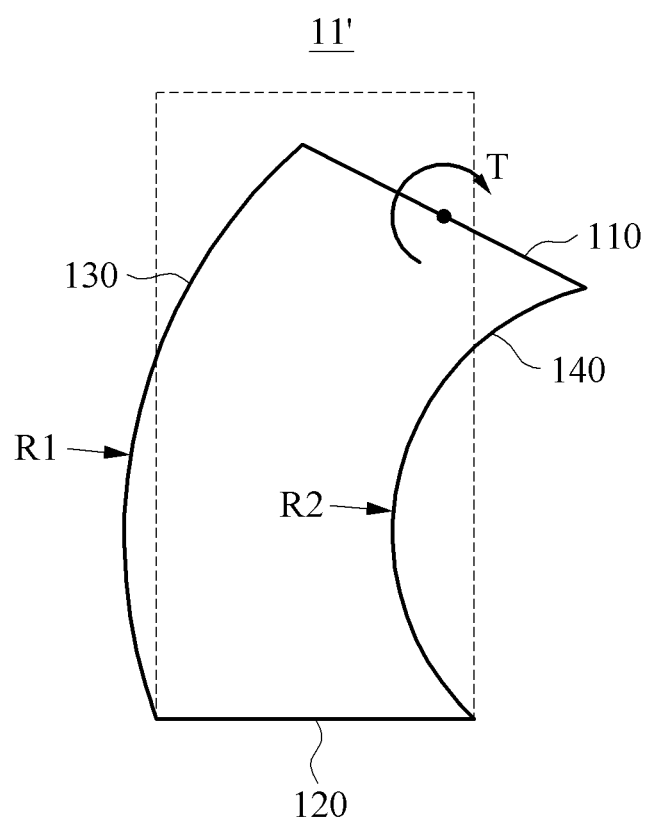
FIG. 4 illustrates an operation of a frame assembly not including distance maintaining members when a torque is applied to an end portion of the frame assembly according to at least one example embodiment.

FIG. 3 illustrates an operation of a frame assembly when a torque is applied to an end portion of the frame assembly according to at least one example embodiment, and FIG. 4 illustrates an operation of a frame assembly not including distance maintaining members when a torque is applied to an end portion of the frame assembly according to at least one example embodiment. FIGS. 3 and 4 illustrate a motion of the frame assembly 11 and a motion of a frame assembly 11', respectively, when a torque is applied to an end portion of the first object 110 in a case in which the first object 110 and the second object 120 move relative to each other, for example, in a case in which the first object 110 is a free end and the second object 120 is a fixed end. Hereinafter, a comparison between the examples of FIGS. 3 and 4 will be described.

Referring to FIG. 4, when a torque T is applied to the first object 110 of the frame assembly 11' not including distance maintaining members, the first longitudinal member 130 may bend at a first curvature R1, and the second longitudinal member 140 may bend at a second curvature R2 that is greater than the first curvature R1, whereby the entire frame assembly 11' may bend. Thus, the frame assembly 11' of FIG. 4 may not perfectly transfer the torque T applied to the first object 110 to the second object 120. That is, only a portion of the torque T may be transferred.

Conversely, in a case of the frame assembly 11 including the distance maintaining members 150 as shown in FIG. 3, a distance between the first longitudinal member 130 and the second longitudinal member 140 may be maintained. The two longitudinal members 130 and 140 may not bend at different curvatures. A torque of the same size as the torque T applied to the first object 110 may be applied to the second object 120 in an opposite direction. Thus, the frame assembly 11 of FIG. 3 may perfectly transfer the torque T applied to the first object 110 to the second object 120. In the above structure, the frame assembly 11 may transfer a torque in both directions.

Figure 5:
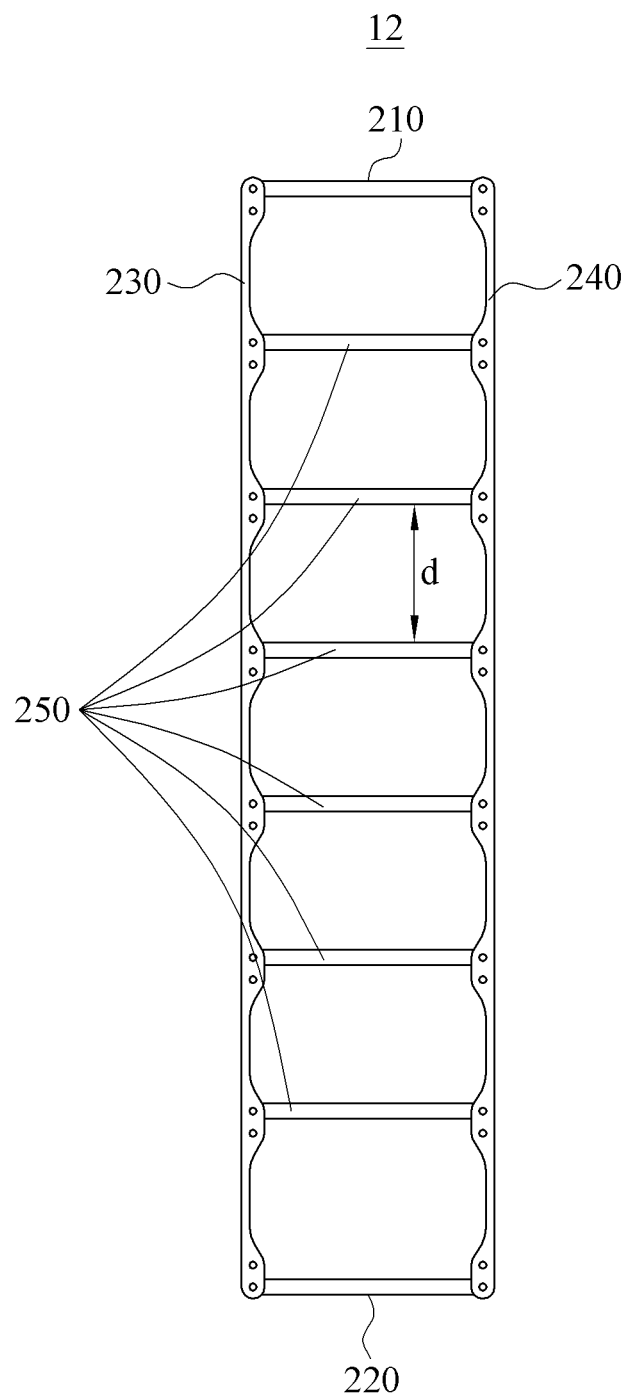
FIG. 5 illustrates a frame assembly according to at least one example embodiment.
Figure 6:
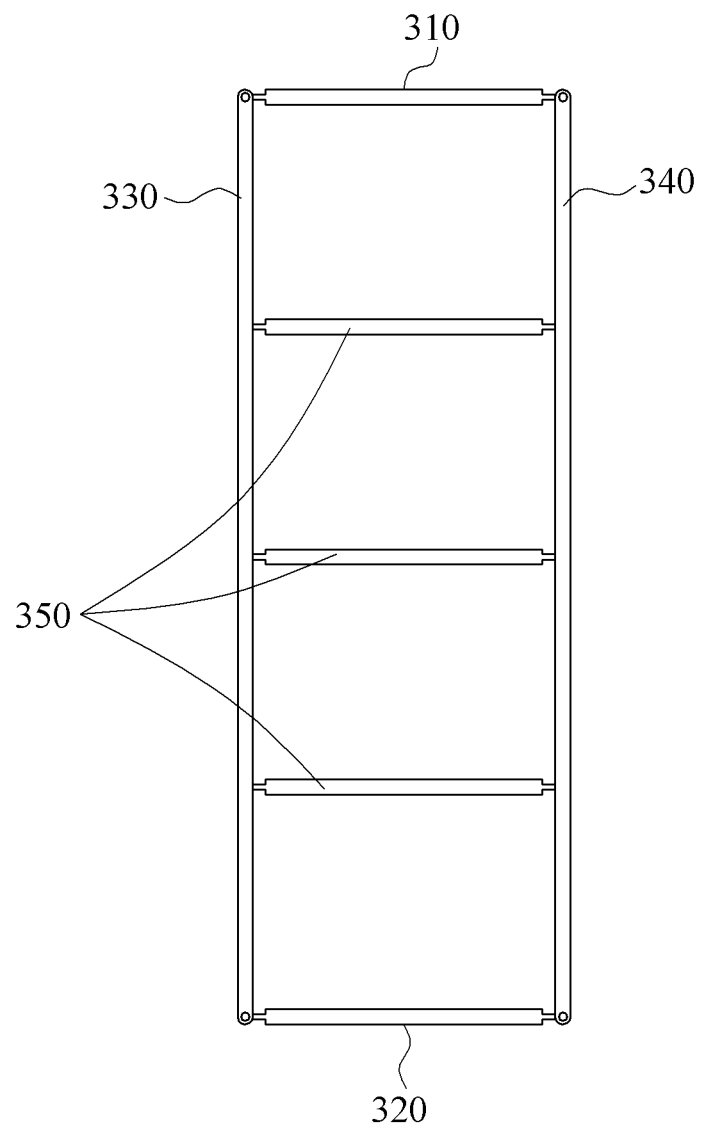
FIG. 6 illustrates a frame assembly according to at least one example embodiment.
Figure 7:
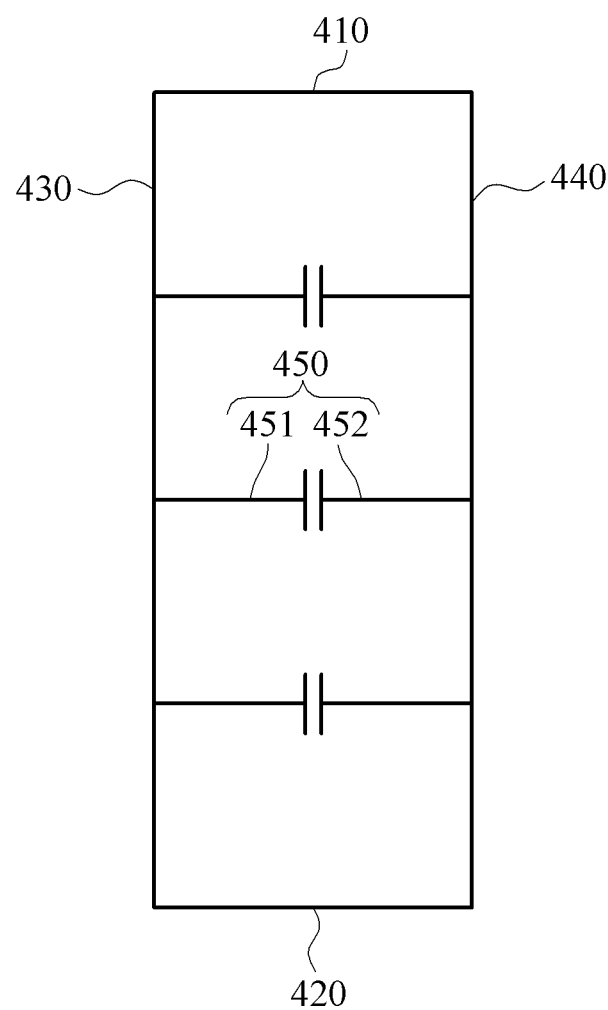
FIG. 7 illustrates a frame assembly according to at least one example embodiment.

FIGS. 5 through 7 illustrate examples of frame assemblies according to at least one example embodiment.

Referring to FIG. 5, a frame assembly 12 may include a first object 210, a second object 220, a first longitudinal member 230, a second longitudinal member 240, and distance maintaining members 250.

Both end portions of the first longitudinal member 230 may be fixed to the first object 210 and the second object 220, respectively. For example, both the end portions of the first longitudinal member 230 may be rotatably hinge-connected to the first object 210 and the second object 220. Similar to both the end portions of the first longitudinal member 230, both end portions of the second longitudinal member 240 may also be fixed to the first object 210 and the second object 220, respectively.

One or both end portions of each distance maintaining member 250 may be rotatably fixed to the first longitudinal member 230 and/or the second longitudinal member 240. In the above structure, the second longitudinal member 240 may maintain substantially the same distance from the first longitudinal member 230 while an intermediate area of the first longitudinal member 230 and an intermediate area of the second longitudinal member 240 may partially slide relative to sides facing each other. FIG. 5 illustrates both the end portions of each distance maintaining member 250 being rotatably hinge-connected to the first longitudinal member 230 and the second longitudinal member 240. The distance maintaining members 250 may include a rigid structure and material.

Referring to FIG. 6, a frame assembly 13 may include a first object 310, a second object 320, a first longitudinal member 330, a second longitudinal member 340, and distance maintaining members 350.

A portion of the distance maintaining members 350 has a flexible structure or material, and thus may bend with respect to the first longitudinal member 330 and the second longitudinal member 340. In the above structure, the second longitudinal member 340 may maintain substantially the same distance from the first longitudinal member 330 while an intermediate area of the first longitudinal member 330 and an intermediate area of the second longitudinal member 340 may partially slide relative to sides facing each other. For example, both end portions of each distance maintaining member 350 may have cross sections that are ⅕ to ¹⁄₁₀ of a cross section of an intermediate area thereof. For example, the intermediate area of each distance maintaining member 350 may have a rigid material or structure.

Unlike FIG. 6, a thickness of each distance maintaining member 350 may be greater than a thickness of the first longitudinal member 330 and a thickness of the second longitudinal member 340. Each distance maintaining member 350 may have a thickness sufficient to prevent buckling of the first longitudinal member 330 and the second longitudinal member 340, for example, a thickness that is 10 to 100 times greater than the thickness of the first longitudinal member 330 and the thickness the second longitudinal member 340.

Figure 8:
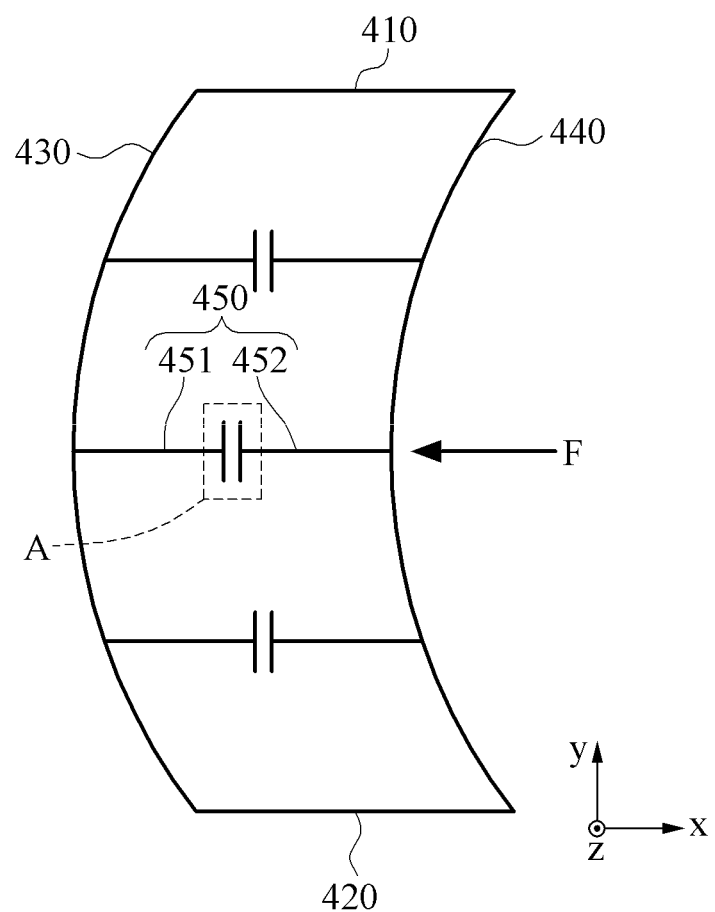
FIG. 8 illustrates an operation of a frame assembly when a force is applied to an intermediate area of the frame assembly in a lateral direction according to at least one example embodiment.

FIG. 7 illustrates a frame assembly according to at least one example embodiment, and FIG. 8 illustrates an operation of the frame assembly when a force is applied to an intermediate area of the frame assembly in a lateral direction according to at least one example embodiment.

Referring to FIGS. 7 and 8, a frame assembly 14 may include a first object 410, a second object 420, a first longitudinal member 430, a second longitudinal member 440, and distance maintaining members 450.

The distance maintaining members 450 may each include a first slider 451 and a second slider 452 configured to slide relative to each other. In the above structure, the second longitudinal member 440 may maintain substantially the same distance from the first longitudinal member 430 while an intermediate area of the first longitudinal member 430 and an intermediate area of the second longitudinal member 440 may partially slide relative to sides facing each other.

The frame assembly 14 may have a flexibility in a direction perpendicular to an intermediate area thereof. When a force F is applied to the intermediate area of the frame assembly 14 as shown in FIG. 8, the first longitudinal member 430 and the second longitudinal member 440 may bend by the force F. In this example, the first longitudinal member 430 and the second longitudinal member 440 may partially slide relative to each other while maintaining the distance therebetween through the distance maintaining members 450. Thus, the first longitudinal member 430 and the second longitudinal member 440 may bend in the same shapes.

Figure 9:
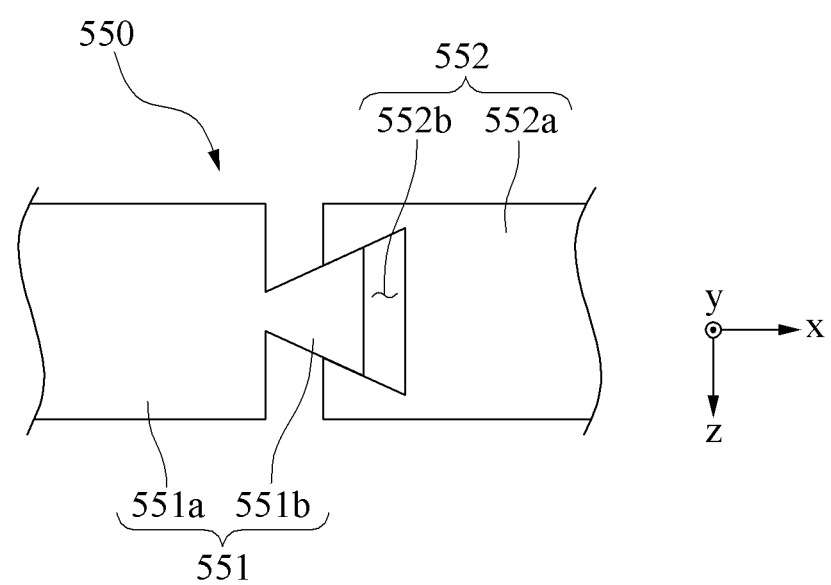
FIG. 9 illustrates a distance maintaining member according to at least one example embodiment.
Figure 10:
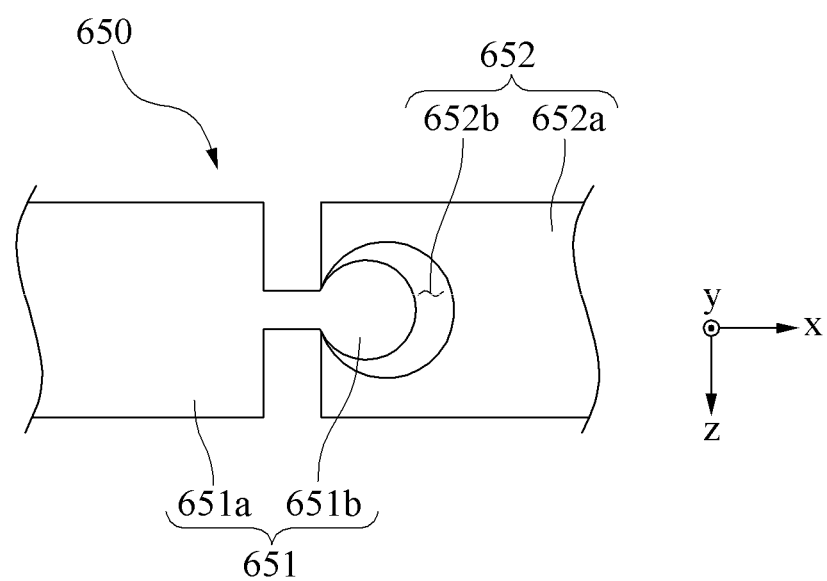
FIG. 10 illustrates a distance maintaining member according to at least one example embodiment.
Figure 11:
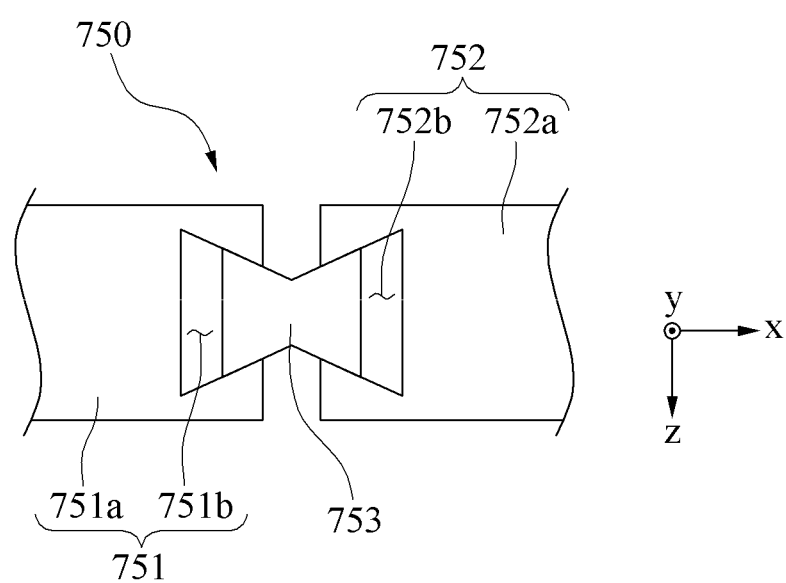
FIG. 11 illustrates a distance maintaining member according to at least one example embodiment.

FIGS. 9 through 11 are examples of distance maintaining members according to at least one example embodiment. FIGS. 9 through 11 are top views of a portion A of FIG. 8, viewed in a negative direction of a y axis.

Referring to FIG. 9, a distance maintaining member 550 may include a first slider 551, and a second slider 552 configured to slide relative to the first slider 551.

The first slider 551 may include a first slider body 551a connected to the first longitudinal member 430 and configured to extend toward the second longitudinal member 440, and a first fitting portion 551b formed on the first slider body 551a. The first slider body 551a and/or the first fitting portion 551b may include a rigid structure and material.

The second slider 552 may include a second slider body 552a connected to the second longitudinal member 440 and configured to extend toward the first longitudinal member 430, and a second fitting portion 552b formed on the second slider body 552a and configured to fit in the first fitting portion 551b. For example, the second slider body 552a and/or the second fitting portion 552b may include a rigid structure and material.

The first slider body 551a and the second slider body 552a may prevent buckling of the first longitudinal member 430 and the second longitudinal member 440 in a direction in which a distance therebetween decreases.

One of the first fitting portion 551b and the second fitting portion 552b may protrude, and the other of the first fitting portion 551b and the second fitting portion 552b may be recessed. The first fitting portion 551b and the second fitting portion 552b may engage with each other, whereby the first slider 551 and the second slider 552 may slide relative to each other without being separated from each other. The first fitting portion 551b may include a portion of which a width increases as a distance from the first slider body 551a increases. For example, the first fitting portion 551b may be provided in a dovetail shape in which a cross section thereof increases toward a protrude direction. The second fitting portion 552b may include a shape in which a cross section of a recess increases toward a recess direction.

Referring to FIG. 10, a distance maintaining member 650 may include a first slider 651 that includes a first slider body 651a and a first fitting portion 651b, and a second slider 652 that includes a second slider body 652a and a second fitting portion 652b.

The first fitting portion 651b may include a portion of which a width increases as a distance from the first slider body 651a increases. For example, the first fitting portion 651b may have a circular cross section, and the second fitting portion 652b may have a cross section corresponding to a recess with two edges bending inward.

Referring to FIG. 11, a distance maintaining member 750 may include a first slider 751 that includes a first slider body 751a and a first fitting portion 751b, a second slider 752 that includes a second slider body 752a and a second fitting portion 752b, and a separation preventing member 753.

The separation preventing member 753 may prevent a separation between the first slider 751 and the second slider 752. One side of the separation preventing member 753 may be coupled to the first fitting portion 751b and slidably move relative to the first fitting portion 751b. For example, the one side of the separation preventing member 753 may be provided in a reversed trapezoidal shape including a portion of which a width increases toward the first slider 751. Similarly, another side of the separation preventing member 753 may be coupled to the second fitting portion 752b. That is, the separation preventing member 753 may be provided in a shape of combination of two reversed trapezoids including portions of which widths increase toward the two sliders 751 and 752, respectively.

Figure 12:
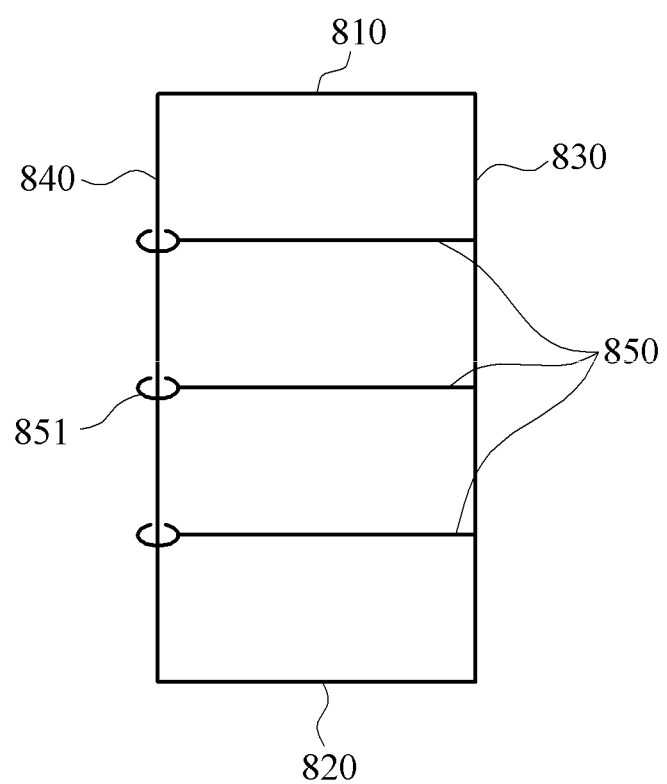
FIG. 12 illustrates a frame assembly according to at least one example embodiment.
Figure 13:
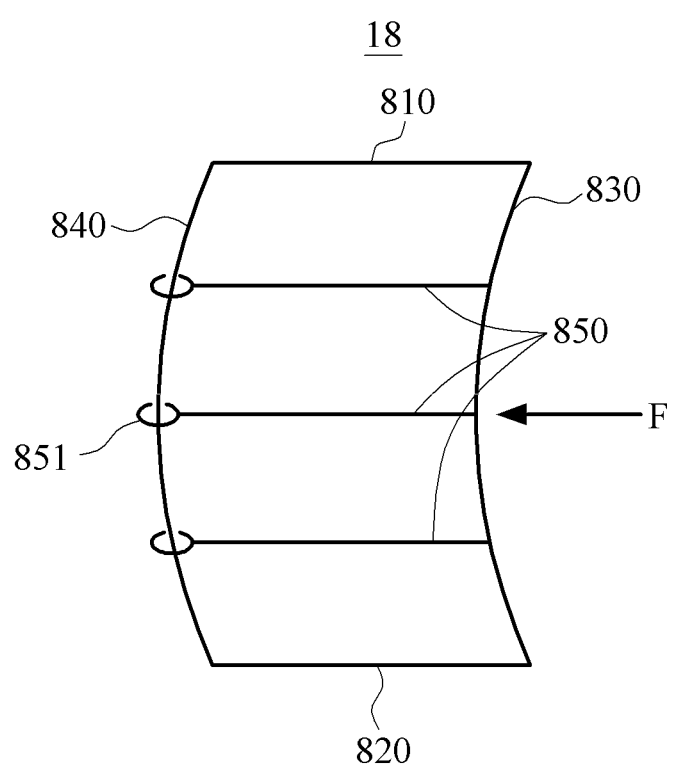
FIG. 13 illustrates an operation of a frame assembly when a force is applied to an intermediate area of the frame assembly in a lateral direction according to at least one example embodiment.

FIG. 12 illustrates a frame assembly according to at least one example embodiment, and FIG. 13 illustrates an operation of the frame assembly when a force is applied to an intermediate area of the frame assembly in a lateral direction according to at least one example embodiment.

Referring to FIGS. 12 and 13, a frame assembly 18 may include a first object 810, a second object 820, a first longitudinal member 830, a second longitudinal member 840, and distance maintaining members 850.

One or both end portions of a distance maintaining member 850 may be slidably connected to the first longitudinal member 830 and/or the second longitudinal member 840. In the above structure, the second longitudinal member 840 may maintain substantially the same distance from the first longitudinal member 830 while an intermediate area of the first longitudinal member 830 and an intermediate area of the second longitudinal member 840 may slide relative to sides facing each other.

FIG. 12 illustrates a state in which one end portion of each distance maintaining member 850 is fixed to the first longitudinal member 830 and another end portion of each distance maintaining member 850 is slidably coupled to the second longitudinal member 840. The distance maintaining member 850 may include a slider 851 configured to slide relative to the second longitudinal member 840. The distance maintaining member 850 may include a rigid structure and material.

As shown in FIG. 13, the frame assembly 18 may be flexible with respect to a force applied to an intermediate area thereof. Thus, when a force F is applied to the intermediate area of the frame assembly 18 in a lateral direction, the first longitudinal member 830 and the second longitudinal member 840 may bend by the force F. In this example, the first longitudinal member 830 and the second longitudinal member 840 may partially slide relative to each other while maintaining a distance therebetween through the distance maintaining members 850. Thus, the first longitudinal member 830 and the second longitudinal member 840 may bend in the same shapes.

A longitudinal member including a flexible material may have a variation with respect to an applied force, the variation increasing as a distance from a fixed end increases according to the principle of the lever. A loss of torque corresponding to the variation may occur, and thus the longitudinal member including the flexible material may not perfectly transfer a torque from one end portion to another end portion. Conversely, a longitudinal member including a rigid material may perfectly transfer a torque from one end portion to another end portion. However, a flexibility of the longitudinal member including the stiff material may decrease at an intermediate portion. The frame assembly according to at least one example embodiment may have a flexible intermediate portion and also perfectly transfer a torque, thereby reducing friction with an object adjacent to the frame assembly and minimizing a loss of torque during a power transfer process.

Figure 14:
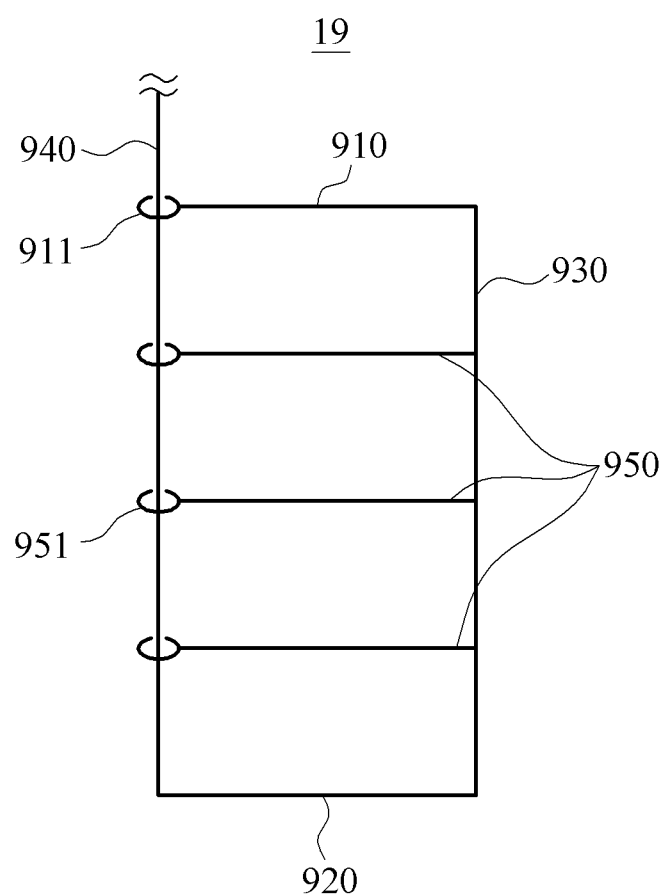
FIG. 14 illustrates an initial state of a frame assembly according to at least one example embodiment.
Figure 15:
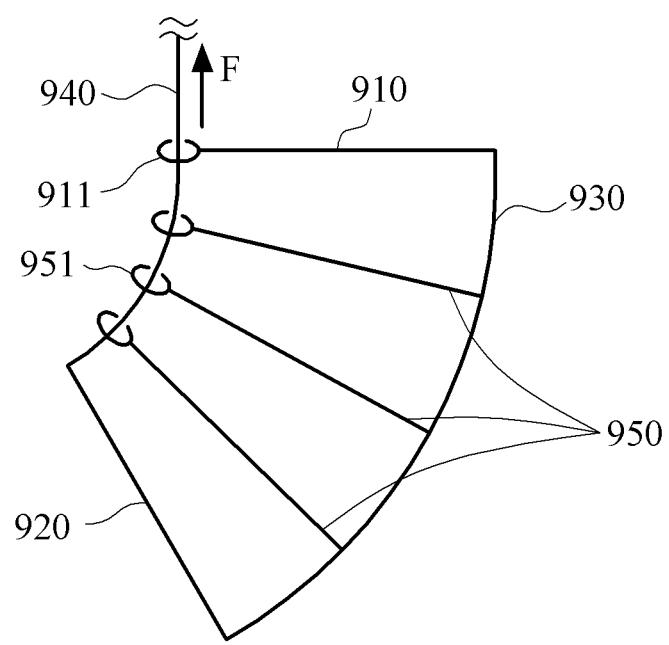
FIG. 15 illustrates an operation of a frame assembly when one of longitudinal members of the frame assembly is pulled according to at least one example embodiment.
Figure 16:
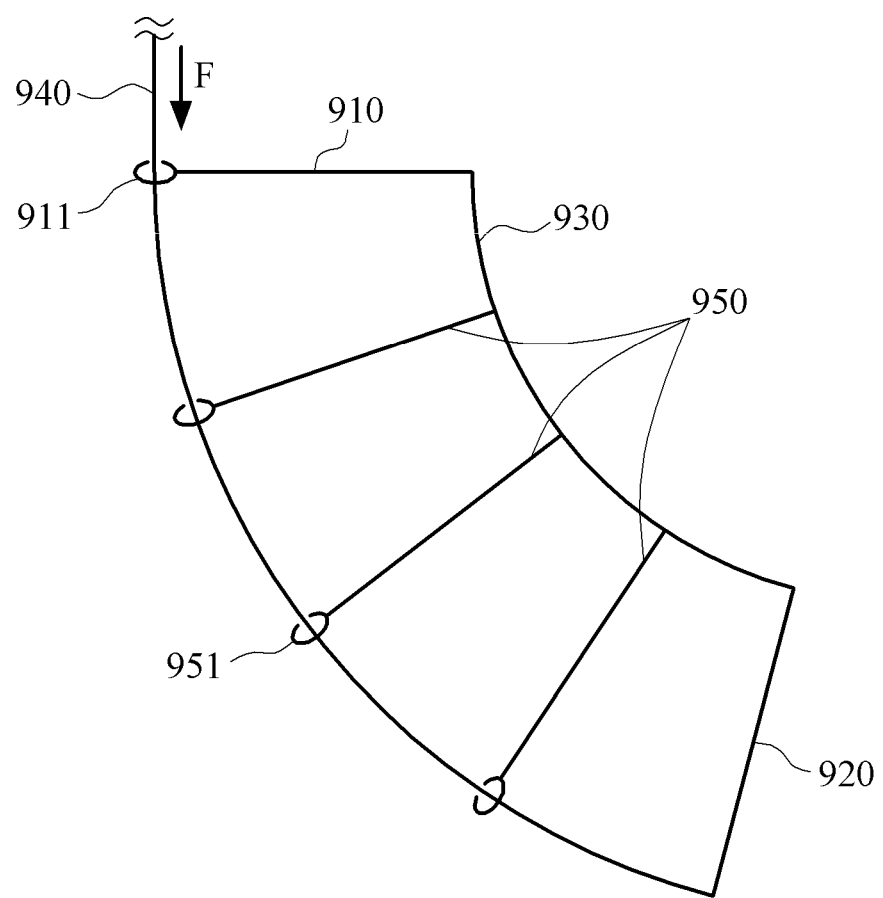
FIG. 16 illustrates an operation of a frame assembly when one of longitudinal members of the frame assembly is pushed according to at least one example embodiment.

FIG. 14 illustrates an initial state of a frame assembly according to at least one example embodiment, FIG. 15 illustrates an operation of the frame assembly when one of longitudinal members of the frame assembly is pulled according to at least one example embodiment, and FIG. 16 illustrates an operation of the frame assembly when one of the longitudinal members of the frame assembly is pushed according to at least one example embodiment.

Referring to FIGS. 14 through 16, a frame assembly 19 may include a first object 910, a second object 920, a first longitudinal member 930, a second longitudinal member 940, and distance maintaining members 950. For example, the first longitudinal member 930 may include an elastic material that restores the original shape when an external force is not applied thereto.

Both ends of the first longitudinal member 930 may be fixed to the first object 910 and the second object 920, respectively. Unlike both the ends of the first longitudinal member 930, one end of the second longitudinal member 940 may be fixed to the second object 920, and another end of the second longitudinal member 940 may be connected to the first object 910 to move relative to the first object 910. The second longitudinal member 940 may be connected to the first object 910 to move in a direction that intersects a longitudinal direction of the first object 910, for example, in a direction perpendicular thereto. Thus, the first object 910 may be slidably connected to the second longitudinal member 940. The first object 910 may include a first slider 911 configured to slide relative to the second longitudinal member 940. For example, the second longitudinal member 940 may penetrate through the first object 910. In this example, a portion of the first object 910 through which the second longitudinal member 940 penetrates may correspond to the first slider 911.

One or both end portions of a distance maintaining member 950 may be slidably connected to the first longitudinal member 930 and/or the second longitudinal member 940. In the above structure, the second longitudinal member 940 may maintain substantially the same distance from the first longitudinal member 930 while an intermediate area of the first longitudinal member 930 and an intermediate area of the second longitudinal member 940 may partially slide relative to sides facing each other. FIG. 14 illustrates a state in which one end portion of each distance maintaining member 950 is fixed to the first longitudinal member 930 and another end portion of each distance maintaining member 950 is slidably coupled to the second longitudinal member 940. The distance maintaining member 950 may include a second slider 951 configured to slide relative to the second longitudinal member 940. The distance maintaining member 950 may include a rigid structure and material.

FIGS. 15 and 16 illustrate an operation of the frame assembly 19 in response to a force applied to the second longitudinal member 940 in a case in which the first object 910 and the second object 920 move relative to each other. For example, the first object 910 may be attached to a thigh of a user and the second object 920 may be attached to a shin of the user such that the first object 910 and the second object 920 may move relative to each other.

Referring to FIG. 15, when a force F to pull the second longitudinal member 940 is applied as shown in FIG. 15, the first longitudinal member 930 and the second longitudinal member 940 may bend in a direction toward the second longitudinal member 940 from on a center of the frame assembly 19. When the tensile force F is applied to the second longitudinal member 940, a torque may be applied to the second object 920 in a clockwise direction in FIG. 15, and a portion of the second object 920 connected to the second longitudinal member 940 may move toward the first object 910. Meanwhile, the frame assembly 19 may have a flexibility in a direction perpendicular to an intermediate area thereof, and the first longitudinal member 930 and the second longitudinal member 940 may partially slide relative to each other while maintaining a distance therebetween through the distance maintaining members 950. Thus, when the tensile force is applied to the second longitudinal member 940, the first longitudinal member 930 and the second longitudinal member 940 may be deformed in similar shapes as shown in FIG. 15. Hence, by the tensile force applied to the second longitudinal member 940, the entire frame assembly 19 may bend in one direction.

Referring to FIG. 16, the second longitudinal member 940 may include a material and structure that is rigid sufficient to prevent buckling with respect to a compressive force applied in a longitudinal direction. In this example, when a force F to push the second longitudinal member 940 is applied as shown in FIG. 16, the first longitudinal member 930 and the second longitudinal member 940 may bend in a direction toward the first longitudinal member 930 from the center of the frame assembly 19. When the compressive force F is applied to the second longitudinal member 940, a torque may be applied to the second object 920 in a counterclockwise direction in FIG. 16, and a portion of the second object 920 connected to the second longitudinal member 940 may move away from the first object 910. The frame assembly 19 may have a flexibility in a direction perpendicular to the intermediate area thereof, and the first longitudinal member 930 and the second longitudinal member 940 may partially slide relative to each other while maintaining the distance therebetween through the distance maintaining members 950. Thus, when the compressive force is applied to the second longitudinal member 940, the first longitudinal member 930 and the second longitudinal member 940 may be deformed in similar shapes as shown in FIG. 16. Hence, by the compressive force applied to the second longitudinal member 940, the entire frame assembly 19 may bend in a direction opposite to the direction of FIG. 15.

In the above structure, an angle between the first object 910 and the second object 920 may be adjusted. Thus, the frame assembly 19 may be used as various types of joint devices. Since the first object 910 and the second object 920 each have a variable center of rotation, the frame assembly 19 may imitate a joint motion of a person or animal having a center of rotation that continuously changes during a rotation motion. Further, since the frame assembly 19 may have a flexibility in a direction perpendicular to the intermediate area thereof, the frame assembly 19 may function as a joint while being deformed flexibly by an external force, thereby reducing an unnecessary load to be applied to a user who is wearing the frame assembly 19.

The second longitudinal member 940 may include using a material and structure that is flexible sufficient to allow buckling with respect to a compressive force applied in a longitudinal direction, for example, a wire. In this example, although the compressive force is applied to the second longitudinal member 940, a torque to rotate the second object 920 may not be applied. In this example, the frame assembly 19 may be deformed only in one direction based on the direction in which the force is applied to the second longitudinal member 940. In detail, when a tensile force is applied to the second longitudinal member 940, the frame assembly 19 may operate as shown in FIG. 15. When the tensile force is released, the frame assembly 19 may restore the initial state as shown in FIG. 14. When a compressive force is applied to the second longitudinal member 940, a remaining portion of the frame assembly 19 except for the second longitudinal member 940 may be maintained without being deformed. In the above structure, the frame assembly 19 may assist a motion of a joint that moves in one direction, for example, a knee joint or an elbow joint.

Figure 17:
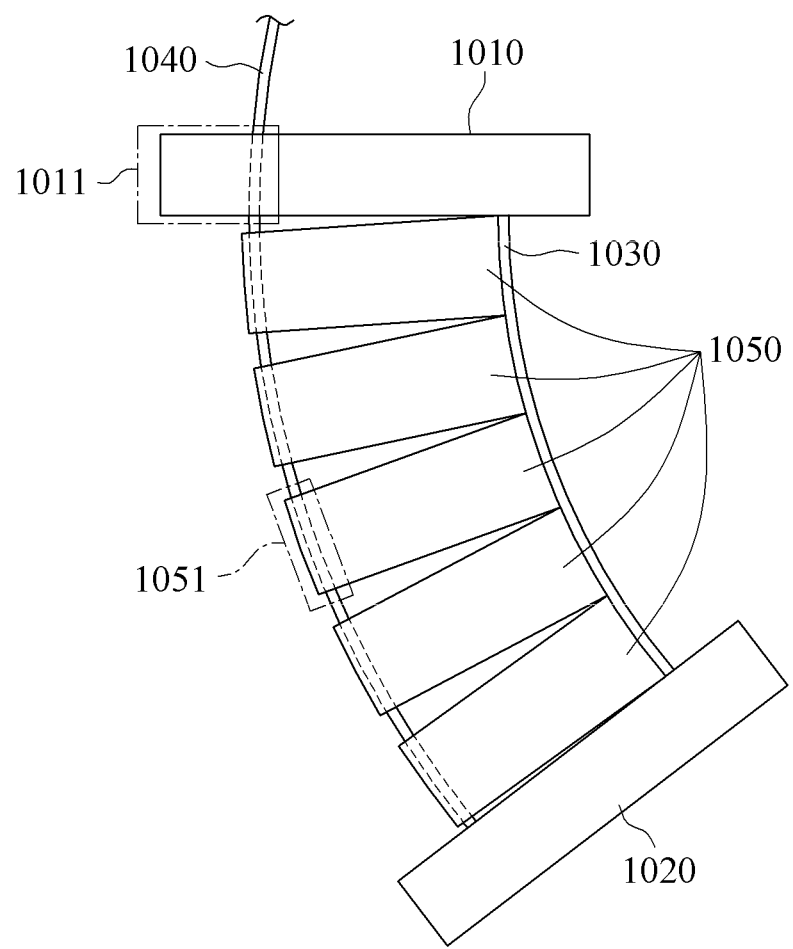
FIG. 17 illustrates an initial state of a frame assembly according to at least one example embodiment.
Figure 18:
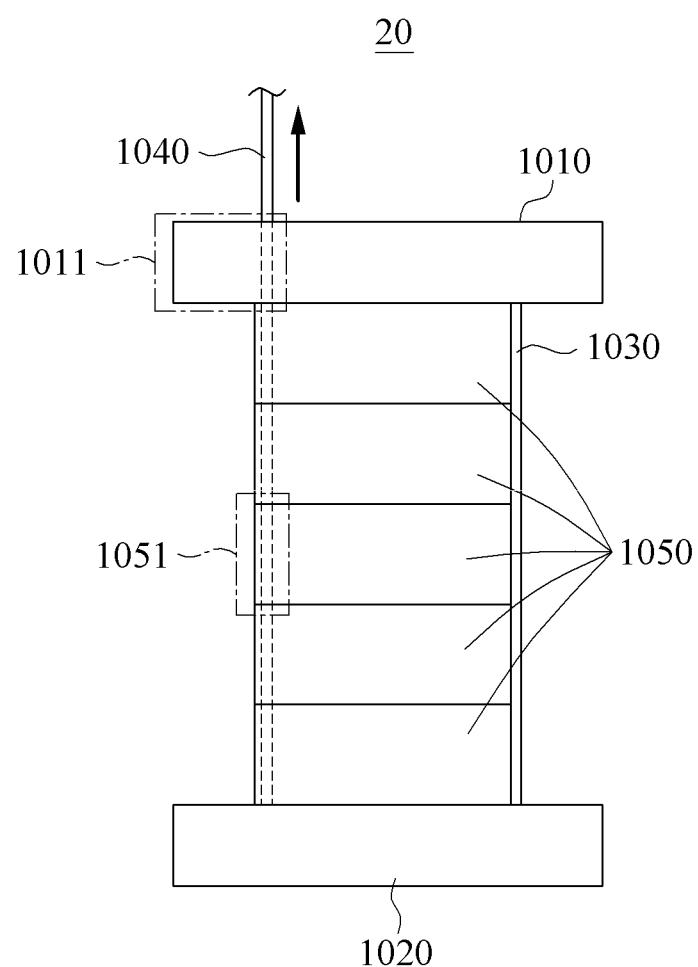
FIG. 18 illustrates an operation of a frame assembly when one of longitudinal members of the frame assembly is pulled according to at least one example embodiment.

FIG. 17 illustrates an initial state of a frame assembly according to at least one example embodiment, and FIG. 18 illustrates an operation of the frame assembly when one of longitudinal members of the frame assembly is pulled according to at least one example embodiment.

Referring to FIGS. 17 and 18, a frame assembly 20 may include a first object 1010, a second object 1020, a first longitudinal member 1030, a second longitudinal member 1040, and a plurality of distance maintaining members 1050.

The first longitudinal member 1030 and the second longitudinal member 1040 may initially have curved shapes when viewed from the front as shown in FIG. 17. For example, the first longitudinal member 1030 may include an elastic material that restores the original shape when an external force is not applied. The first object 1010 may include a first slider 1011 configured to slide relative to the second longitudinal member 1040. A distance maintaining member 1050 may include a second slider 1051 configured to slide relative to the second longitudinal member 1040.

Both end portions of the first longitudinal member 1030 may be fixed to the first object 1010 and the second object 1020, respectively. The first longitudinal member 1030 may include a material that is flexible while having a stiffness sufficient to prevent buckling by a self-weight, for example, a material such as synthetic resin. For example, the first longitudinal member 1030 may be provided in a shape of a plate with a side facing the second longitudinal member 1040.

One end portion of the second longitudinal member 1040 may be fixed to the second object 1020, and another end portion of the second longitudinal member 1040 may be connected to the first object 1010 to move in a direction intersecting a longitudinal direction of the first object 1010. The second longitudinal member 1040 may include a flexible material, and need not necessarily have a stiffness sufficient to prevent buckling. For example, the second longitudinal member 1040 may be a cable to be inserted into recesses or holes formed in the first slider 1011 and the second slider 1051.

In the above structure, the frame assembly 20 may be used as a motion assistance device for a joint that performs a flexion motion as shown in FIG. 17 or an extension motion as shown in FIG. 18.

The flexion motion or the extension motion may be performed by a force applied to the second longitudinal member 1040. For example, in a case in which the first longitudinal member 1030 is an elastic body and has an initial state as shown in FIG. 17, the extension motion as shown in FIG. 18 may be performed when the second longitudinal member 1040 is pulled, and the flexion motion as shown in FIG. 17 may be performed by an elastic restoring force when the force to pull the second longitudinal member 1040 is released.

By adjusting heights of the plurality of distance maintaining members 1050, a maximum extension angle of the frame assembly 20 may be restricted. For example, in the structure as shown in FIGS. 17 and 18, the maximum extension angle of the frame assembly 20 may be restricted not to exceed 180 degrees.

Figure 19:
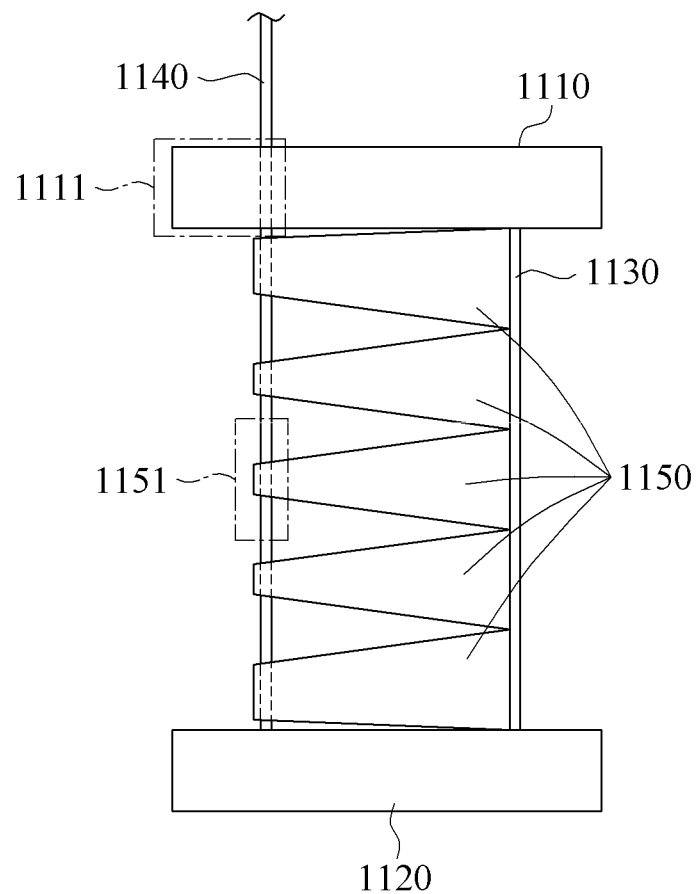
FIG. 19 illustrates an initial state of a frame assembly according to at least one example embodiment.
Figure 20:
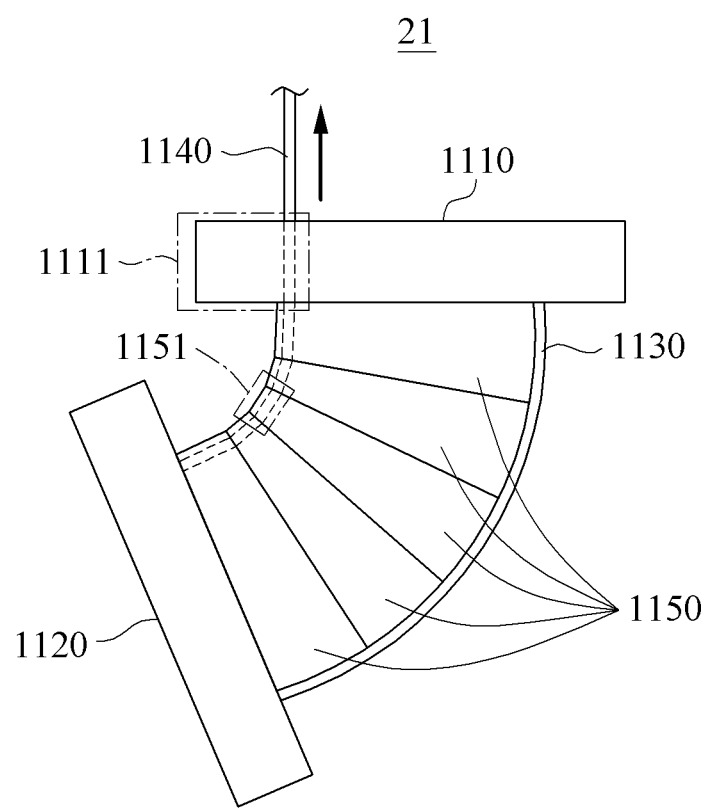
FIG. 20 illustrates an operation of a frame assembly when one of longitudinal members of the frame assembly is pulled according to at least one example embodiment.

FIG. 19 illustrates an initial state of a frame assembly according to at least one example embodiment, and FIG. 20 illustrates an operation of the frame assembly when one of longitudinal members of the frame assembly is pulled according to at least one example embodiment.

Referring to FIGS. 19 and 20, a frame assembly 21 may include a first object 1110, a second object 1120, a first longitudinal member 1130, a second longitudinal member 1140, and a plurality of distance maintaining members 1150. The first object 1110 and each distance maintaining member 1150 may include a first slider 1111 and a second slider 1151, respectively.

The first longitudinal member 1130 and the second longitudinal member 1140 may initially have straight shapes when viewed from the front as shown in FIG. 19.

As shown in FIG. 20, when a tensile force is applied to the second longitudinal member 1140, the frame assembly 20 may perform a flexion motion. As shown in FIG. 19, when the tensile force applied to the second longitudinal member 1140 is released, the frame assembly 20 may perform an extension motion.

A height of at least one of the plurality of distance maintaining members 1150 may decrease from the first longitudinal member 1130 toward the second longitudinal member 1140. For example, at least one of the plurality of distance maintaining members 1150 may be provided in a trapezoidal shape. A portion corresponding to a bottom base of the trapezoidal shape may be fixed to the first longitudinal member 1130, and a portion corresponding to a top base of the trapezoidal shape may be slidably connected to the second longitudinal member 1140. A height of a portion of at least one distance maintaining member 1150 connected to the second longitudinal member 1140 may less than a height of a portion of the at least one distance maintaining member 1150 connected to the first longitudinal member 1130. For example, the at least one distance maintaining member 1150 may have a wedge shape with a height decreasing toward the second longitudinal member 1140. In the above structure, a maximum flexion angle of the frame assembly 21 may be restricted.

Figure 21:
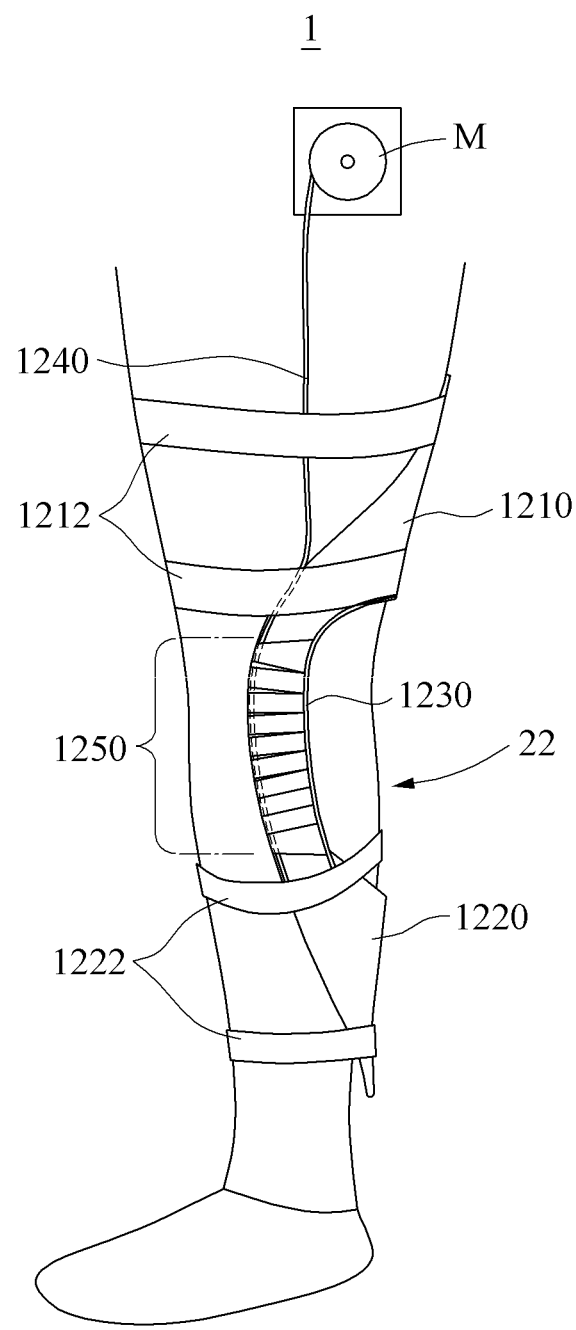
FIG. 21 is a side view illustrating a motion assistance apparatus according to at least one example embodiment.
Figure 22:
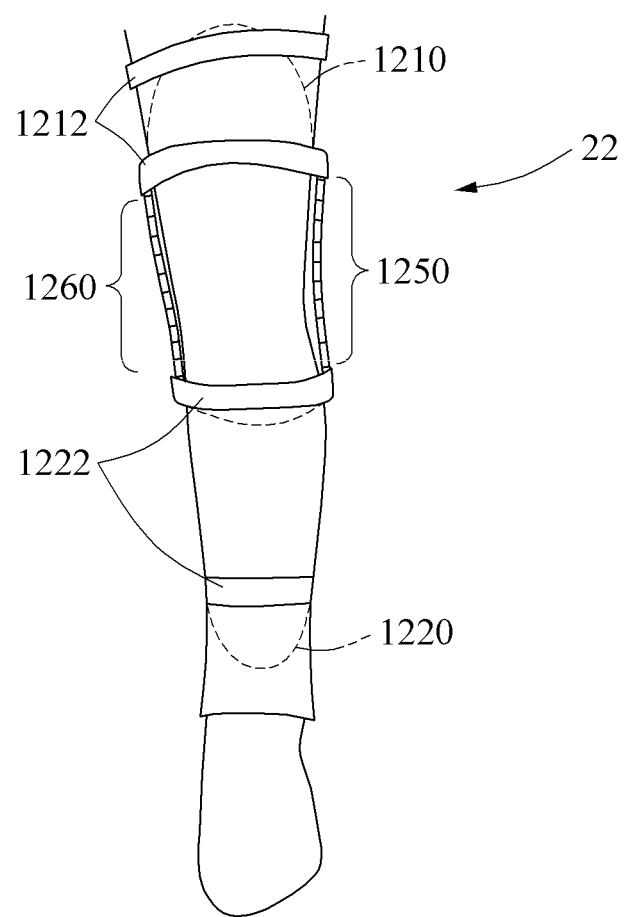
FIG. 22 is a front view illustrating a motion assistance apparatus according to at least one example embodiment.

FIG. 21 is a side view illustrating a motion assistance apparatus according to at least one example embodiment, and FIG. 22 is a front view illustrating the motion assistance apparatus according to at least one example embodiment.

Referring to FIGS. 21 and 22, a motion assistance apparatus 1 may be worn by a user to assist a motion of the user. The user may correspond to a human, an animal, or a robot. However, the user is not limited thereto. Although FIGS. 21 and 22 illustrate a case in which the motion assistance apparatus 1 assists a motion of a knee of the user, the motion assistance apparatus 1 may also assist a motion of another portion in an upper body, for example, a wrist or an elbow of the user, or a motion of another portion in a lower body, for example, an ankle of the user. The motion assistance apparatus 1 may assist a motion of a portion of the user. Hereinafter, a case in which the motion assistance apparatus 1 assists a motion of a knee of a human will be described. However, example embodiments are not limited thereto.

The motion assistance apparatus 1 may include a first wearable portion 1212 and a second wearable portion 1222 that are disposed on opposite sides from a joint of the user, a frame assembly 22 connected between the first wearable portion 1212 and the second wearable portion 1222, and an actuator M to operate the frame assembly 22.

The first wearable portion 1212 may support a portion of the user. The first wearable portion 1212 may include, for example, a detachable belt to support the entire circumference of a thigh above the knee of the user. Similarly, the second wearable portion 1222 may also include a belt to support a circumference of a shin above the ankle of the user. The first wearable portion 1212 and the second wearable portion 1222 may fix a first object 1210 and a second object 1220 of the frame assembly 22 to a body of the user.

For ease of description, the first wearable portion 1212 and the first object 1210 are illustrated as separate elements. However, the first wearable portion 1212 and the first object 1210 may be provided as an integral body. Further, the first object 1210 may perform the function of the first wearable portion 1212. The above description may also apply to the second wearable portion 1222 and the second object 1220.

The frame assembly 22 may transfer, to the user, a torque to relatively rotate the thigh and a calf connected to the knee joint of the user. The frame assembly 22 may include a first longitudinal member 1230 fixed to the first object 1210 and the second object 1220, a second longitudinal member 1240 slidably connected to the first object 1210 and fixed to the second object 1220, and a plurality of first distance maintaining members 1250. The second longitudinal member 1240 may operate to be wound or unwound on an outer circumferential surface of a rotary body rotated by the actuator M.

The frame assembly 22 may further include a third longitudinal member (not shown) configured to connect the first object 1210 and the second object 1220 and disposed on an opposite side of the first longitudinal member 1230 from the knee joint of the user, a fourth longitudinal member (not shown) configured to connect the first object 1210 and the second object 1220 and disposed on an opposite side of the second longitudinal member 1240 from the knee joint of the user, and second distance maintaining members 1260 fixed to the third longitudinal member and slidably connected to the fourth longitudinal member. The fourth longitudinal member may operate to be wound or unwound on the outer circumferential surface of the rotary body rotated by the actuator M. It is possible to assist a motion of a joint more stably using the frame assembly 22 provided in a structure having symmetry on both sides from a single joint. Meanwhile, the fourth longitudinal member may be connected to another actuator, rather than the actuator M to which the second longitudinal member 1240 is connected, thereby operating independently of the second longitudinal member 1240.

The actuator M may be connected to the second longitudinal member 1240 and/or the fourth longitudinal member, and operate the frame assembly 22. The actuator M may be attached directly to the user, or indirectly to the user by being fixed to a portion of the motion assistance apparatus 1. In another example embodiment, the actuator M may be carried by the user, rather than being fixed separately. A position of the actuator M is not limited thereto.

Hereinafter, a case in which the frame assembly 22 has a flexion state as an initial state, as shown in FIG. 17, will be described. The frame assembly 22 may perform a flexion motion or an extension motion based on a direction in which the rotary body is rotated by the actuator M.

Figure 24:
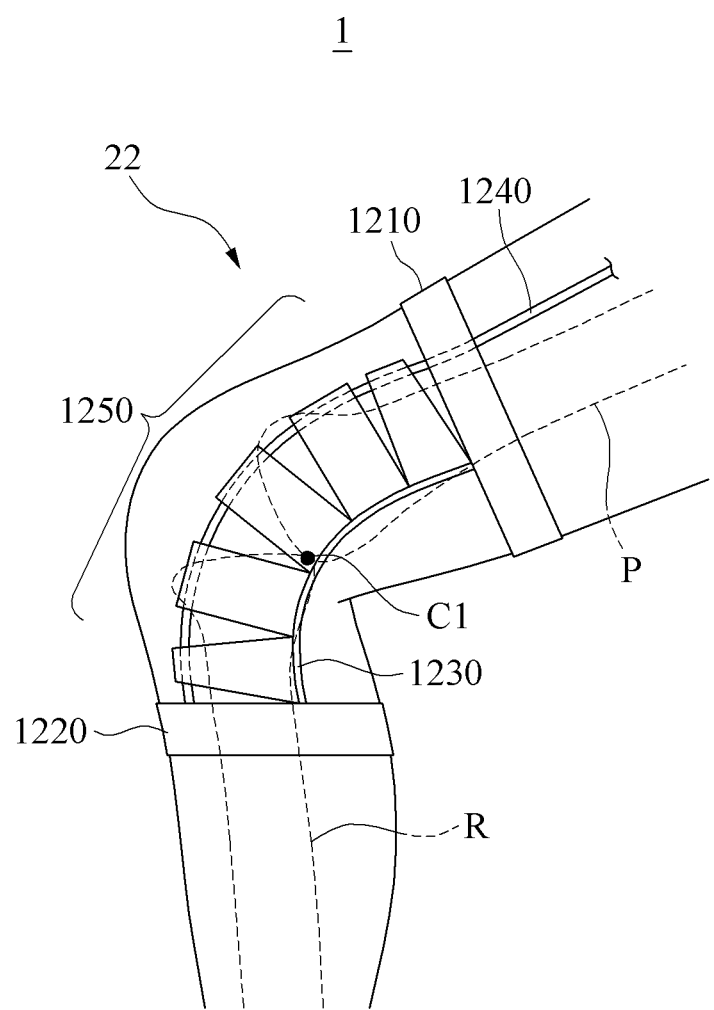
FIG. 24 illustrates a shape of a frame assembly when a knee of a user is in a flexion state according to at least one example embodiment.

When the rotary body rotates in a clockwise direction in FIG. 21 while the knee the user is in a flexion state as shown in FIG. 24, the second longitudinal member 1240 and/or the fourth longitudinal member may be pulled, and a torque to rotate the second object 1220 relative to the first object 1210 in a clockwise direction may be applied to the second object 1220. Through the above operation, the frame assembly 22 may perform the extension motion, and thus the motion assistance apparatus 1 may assist the user to extend a leg, for example, to stand up. By transferring a sufficient power to the actuator M, the motion assistance apparatus 1 may help the user to continuously stand erect. By wedge shapes of the first distance maintaining members 1250 and/or the second distance maintaining members 1260, a maximum extension angle of the frame assembly 22 may be restricted not to exceed a maximum extension angle of the knee joint of the user. Thus, although a power exceeding a power to maintain the user to stand erect is applied to the second longitudinal member 1240, damage to the knee joint of the user may be prevented.

Conversely, when the rotary body rotates in a counterclockwise direction while the knee of the user is in an extension state as shown in FIG. 21, the second longitudinal member 1240 may be released and a magnitude of the torque applied to the second object 1220 may be reduced. In this example, by an elastic restoring force of the first longitudinal member 1230 and/or the third longitudinal member, a torque to rotate the second object 1220 relative to the first object 1210 in a counterclockwise direction may be applied to the second object 1220. Through the above operation, the frame assembly 22 may perform a flexion motion. Thus, the motion assistance apparatus 1 may assist the user to bend a leg, for example, to sit down. Meanwhile, the frame assembly 22 may have a flexion state as an initial state, and thus the actuator M may not need to operate while the user is sitting, whereby energy may be saved.

The frame assembly 22 of the motion assistance apparatus 1 may be flexible with respect to a force applied in a lateral direction as described above, and thus may be deformed to be suitable for changes in a body shape of the user corresponding to various motion states. Thus, although the frame assembly 22 is in close contact with the user, negative effects on wearability may be minimized. Since the frame assembly 22 may not need to be designed to be spaced apart from a body of the user to prevent an issue of friction, a space required to install the frame assembly 22 may be reduced and the entire motion assistance apparatus 1 may be worn under clothing.

Meanwhile, a portion of joints of the user may simultaneously roll and slide, and thus a simple ball joint type may not prevent a misalignment and transfer an unnecessary load to the user. That is, since a center of rotation of an actual joint of the user changes, whereas a center of rotation of a ball joint is fixed, conventionally, the unnecessary load may be transferred to the user due to the misalignment. The unnecessary load may decrease a user wearability, and cause deformation of the ball joint and components connected to the ball joint. Hereinafter, the misalignment will be described in detail based on a knee joint of a human body, and advantages of using a frame assembly according to at least one example embodiment as a joint device will be described.

Figure 23:
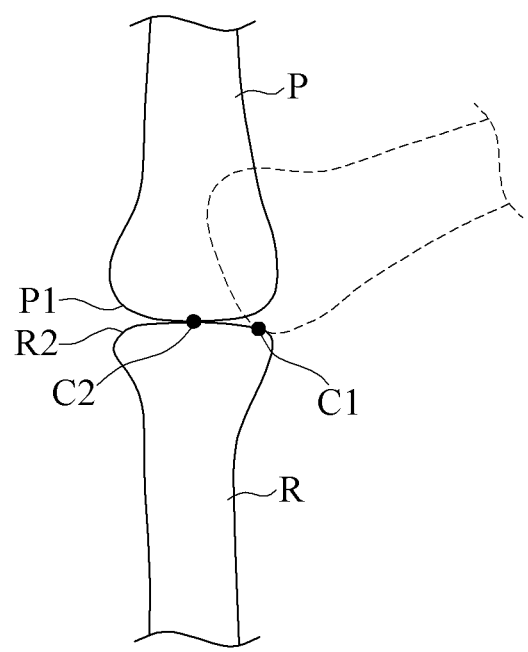
FIG. 23 illustrates a flexion motion of a knee joint of a user.

FIG. 23 illustrates a flexion motion of a knee joint of a user.

Referring to FIG. 23, a knee joint of a user may simultaneously perform a rolling motion and a sliding motion while the user bends and stretches a knee. When a thigh or a calf of the user pivots about the knee joint, a center of rotation of the knee joint of the user may change. For example, a thighbone P may perform a rolling motion on a shin bone R. In conjunction with the rolling motion, an end surface P1 of the thighbone P may slide along an end surface R1 of the shin bone R. Thus, a center of rotation of the rolling motion of the thighbone P may change from an initial contact point C1 to a subsequent contact point C2.

As shown in FIG. 23, the center of rotation of the actual joint of the user may change during a motion process, and thus the simple ball joint type may not imitate such a motion exactly. However, a center of rotation of a frame assembly according to at least one example embodiment is not fixed unlike the ball joint type, and thus may be used to imitate the motions of the actual joint. Hereinafter, descriptions will be provided further with reference to the drawings.

Figure 25:
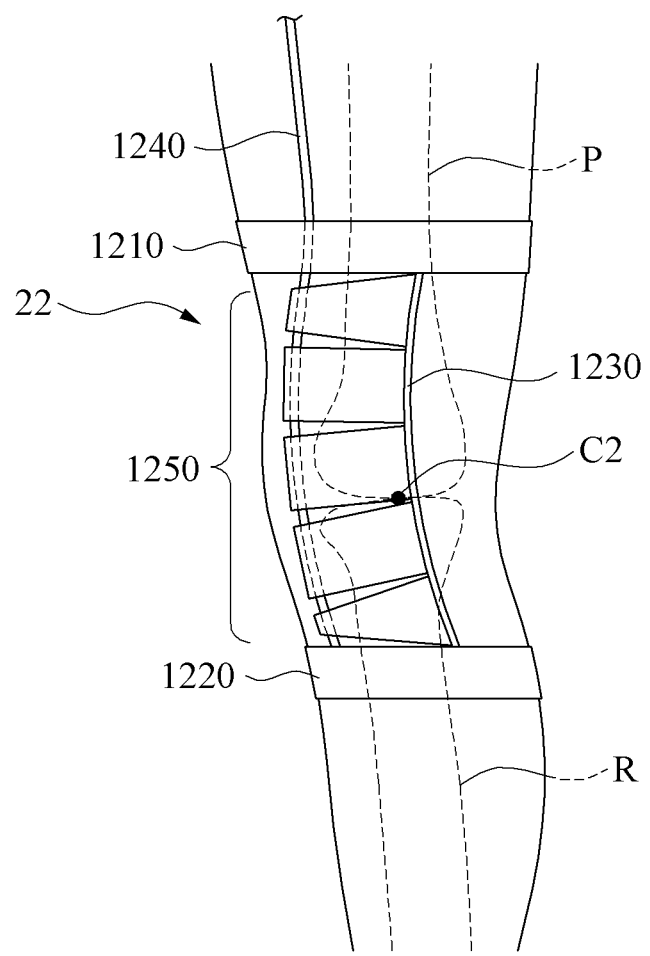
FIG. 25 illustrates a shape of a frame assembly when a knee of a user is in an extension state according to at least one example embodiment.

FIG. 24 illustrates a shape of a frame assembly when a knee of a user is in a flexion state according to at least one example embodiment, and FIG. 25 illustrates a shape of the frame assembly when the knee of the user is in an extension state according to at least one example embodiment. Hereinafter, the first object 1210 may perform the function of the first wearable portion 1212 of FIG. 21, and the second object 1220 may perform the function of the second wearable portion 1222 of FIG. 21.

Referring to FIGS. 24 and 25, the frame assembly 22 may include the plurality of distance maintaining members 1250. Each distance maintaining member 1250 may rotate relative to another adjacent distance maintaining member 1250, and thus the frame assembly 22 may have a plurality of centers of rotation corresponding to a number of the distance maintaining members 1250. Further, since the frame assembly 22 has a flexibility with respect to a force applied in a lateral direction, the frame assembly 22 may be self-deformed to a shape that reduces (or, alternatively, minimizes) an internal stress, by the external force applied to the frame assembly 22. Thus, the frame assembly 22 may be self-aligned such that a momentary center of rotation between the first object 1210 and the second object 1220 may match a momentary center of rotation of a knee joint of the user.

When the knee of the user is in a flexion state as shown in FIG. 24, the center of rotation of the knee joint may be the contact point C1 as shown in FIG. 23. When the user moves in a state in which the center of rotation of the frame assembly 22 does not match the contact point C1, a misalignment may cause an external force to be applied to the frame assembly 22. The external force may deform the frame assembly 22 which is flexible with respect to a force applied in a lateral direction, thereby matching the center of rotation between the first object 1210 and the second object 1220 with the contact point C1.

Similarly, when the knee of the user is in an extension state as shown in FIG. 25, the center of rotation of the knee joint may change to the contact point C2 as shown in FIG. 23. In this example, the external force applied to the frame assembly 22 may change. The external force may deform the frame assembly 22, thereby matching the center of rotation between the first object 1210 and the second object 1220 with the contact point C2.

The frame assembly 22 may have a flexibility and a multi-degree of freedom through the flexible first longitudinal member 1230, the second longitudinal member 1240, and the plurality of distance maintaining members 1250, and thus may solve an issue of misalignment.

Figure 26:
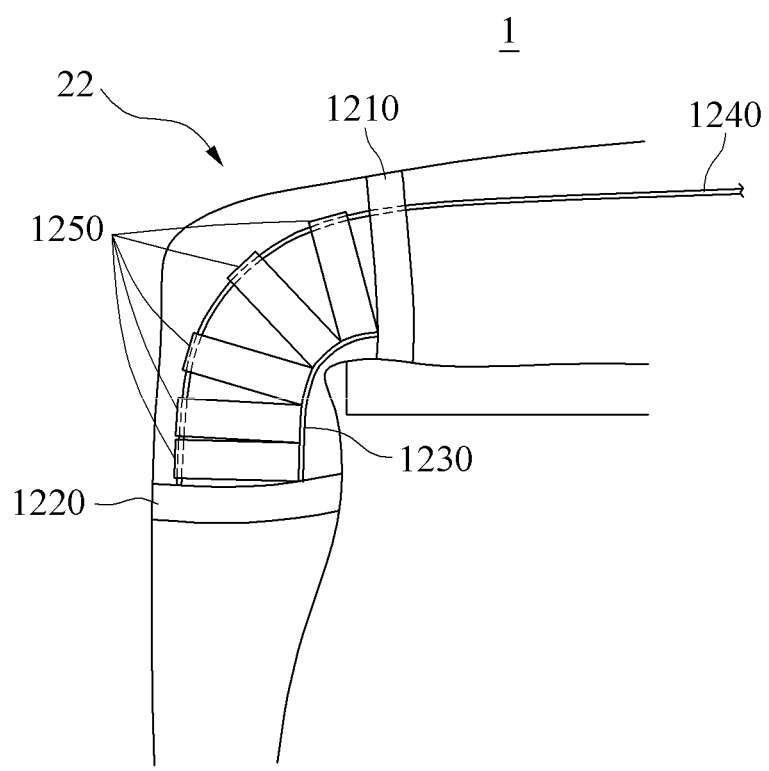
FIG. 26 illustrates a frame assembly being worn by a user according to at least one example embodiment.
Figure 27:
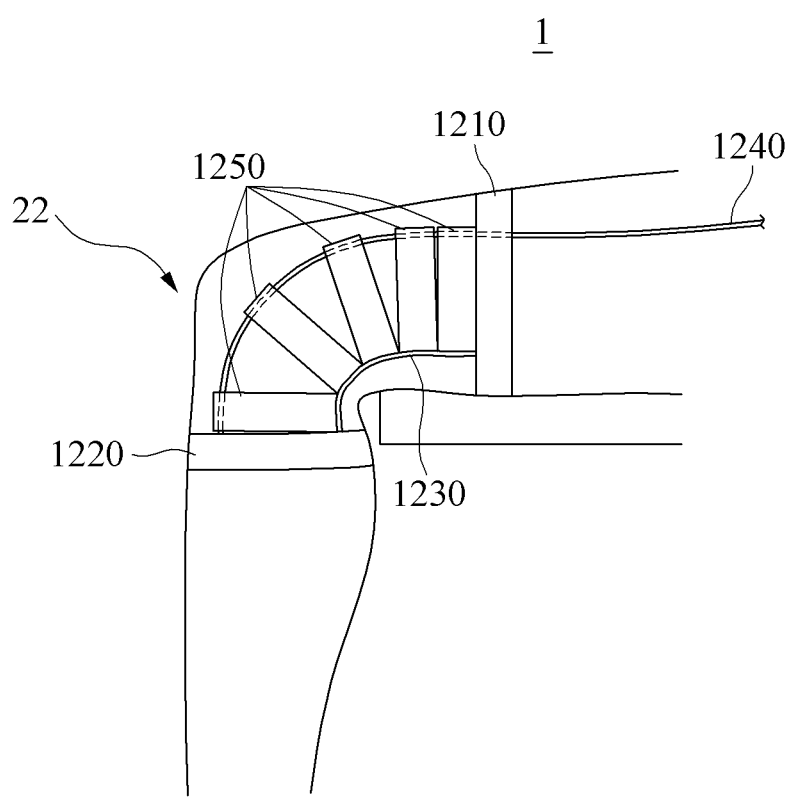
FIG. 27 illustrates a frame assembly being worn by a user at a position different from a position shown in FIG. 24 according to at least one example embodiment.

FIG. 26 illustrates a frame assembly being worn by a user according to at least one example embodiment, and FIG. 27 illustrates the frame assembly being worn by the user at a position different from a position shown in FIG. 24 according to at least one example embodiment.

For example, to utilize the plurality of distance maintaining members 1250 uniformly, a center of the frame assembly 22 may be matched with a joint of a user. However, referring to FIGS. 26 and 27, the frame assembly 22 may perfectly operate without causing a misalignment simply through rough positioning.

Referring to FIG. 26, the center of the frame assembly 22 is positioned on a lower side than the joint. In this example, a gap between distance maintaining members 1250 positioned relatively close to an upper body of the user may increase further, whereby the frame assembly 22 may operate normally as a joint device.

Referring to FIG. 27, the center of the frame assembly 22 is positioned on an upper side than the joint. In this example, a gap between distance maintaining members 1250 positioned relatively close to a lower body of the user may increase further, whereby the frame assembly 22 may operate normally as a joint device.

A motion assistance apparatus including a general rotary joint faces a decrease in wearability and damage to the apparatus due to a misalignment when an axis of rotation of the rotary joint does not match an axis of rotation of a joint of a user. However, the motion assistance apparatus 1 may be worn on any portion of the user, and thus may be worn easily.

Figure 28:
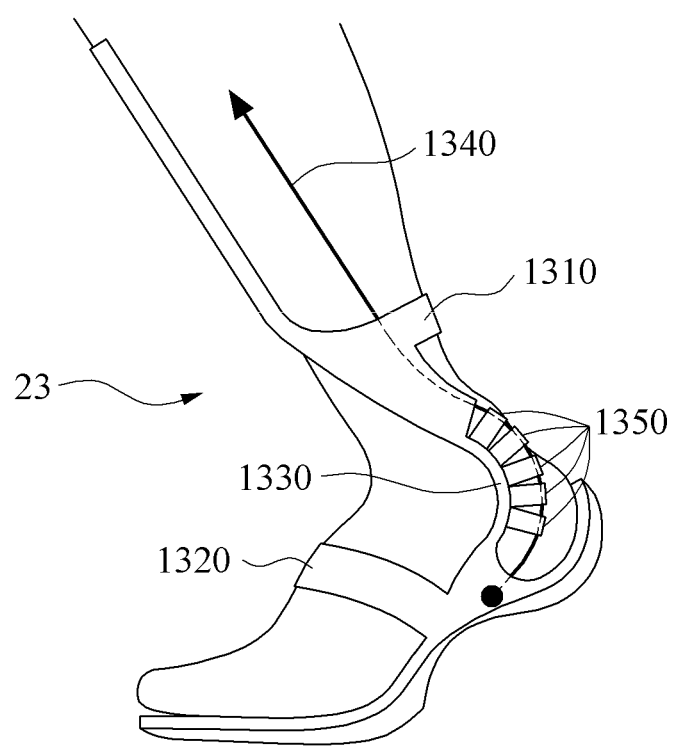
FIG. 28 illustrates a motion assistance apparatus according to at least one example embodiment.

FIG. 28 illustrates a motion assistance apparatus according to at least one example embodiment.

Referring to FIG. 28, a motion assistance apparatus 2 may assist a motion of an ankle joint. The motion assistance apparatus 2 may include a first object 1310 configured to support a portion of a user, for example, a front side of a shin, a second object 1320 configured to support another portion of the user, for example, a sole, and a frame assembly 23 that includes a first longitudinal member 1330 configured to connect the first object 1310 and the second object 1320, a second longitudinal member 1340 spaced apart from the first longitudinal member 1330, and a plurality of distance maintaining members 1350 connected between the first longitudinal member 1330 and the second longitudinal member 1340.

When the second longitudinal member 1340 is pulled, a gap between the plurality of distance maintaining members 1350 may decrease and the second object 1320 may rotate relative to the first object 1310 in a counterclockwise direction, whereby the user may perform a push-off motion. Conversely, when a force to pull the second longitudinal member 1340 is released, the gap between the plurality of distance maintaining members 1350 may increase by an elastic restoring force of the first longitudinal member 1330, whereby the user may return to the original state.

Meanwhile, an axis of rotation of a portion of joints of the user may change based on an eversion motion or an inversion motion. A simple ball joint type may not prevent a misalignment and transfer an unnecessary load to the user. Hereinafter, the misalignment will be described in detail based on an ankle joint of a human body, and advantages of using a frame assembly according to at least one example embodiment as a joint device will be described.

Figure 29:
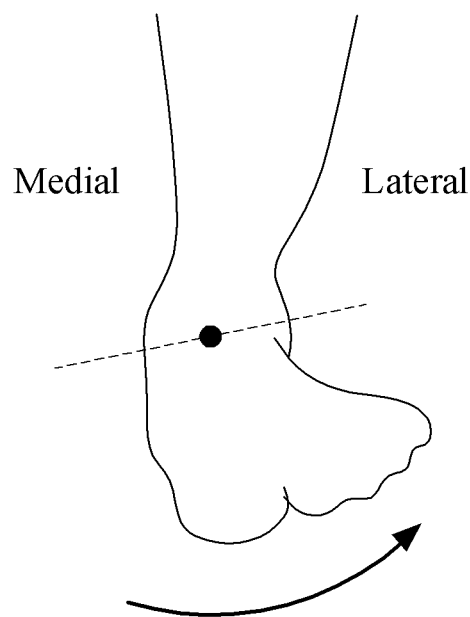
FIG. 29 illustrates an eversion motion of an ankle joint of a user.
Figure 30:
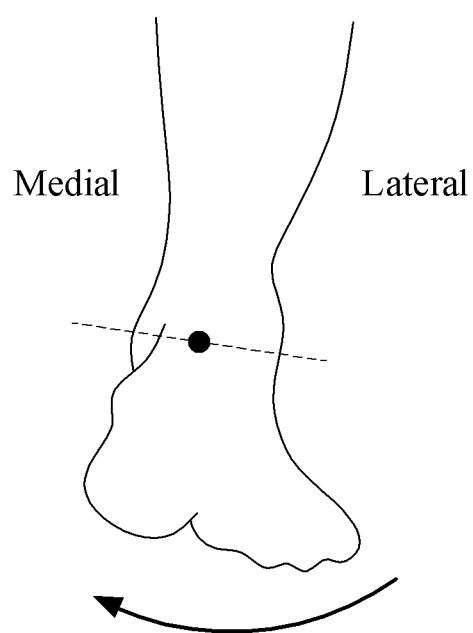
FIG. 30 illustrates an inversion motion of an ankle joint of a user.

FIG. 29 illustrates an eversion motion of an ankle joint of a user, and FIG. 30 illustrates an inversion motion of the ankle joint of the user.

Referring to FIGS. 29 and 30, an ankle of the user may perform an eversion motion that bends outward from a center of the user, and an inversion motion that bends inward from the center of the user. Based on the motions, axes of rotation of a flexion motion and an extension motion of the ankle may change as well. In detail, when the ankle performs the eversion motion as shown in FIG. 29, the axes of rotation of the flexion/extension motions of the ankle may change to slant downward toward the center of the user. Conversely, when the ankle performs the inversion motion as shown in FIG. 30, the axes of rotation of the flexion/extension motions of the ankle may change to slant upward toward the center of the user.

As shown in FIGS. 29 and 30, a center of rotation of an actual joint of a user may change during a motion process, and thus the simple ball joint type may not imitate such a motion exactly. However, a center of rotation of the frame assembly 23 is not fixed unlike the ball joint type, and thus may be used to imitate the motions of the actual joint. Hereinafter, descriptions will be provided further with reference to the drawings.

Figure 31:
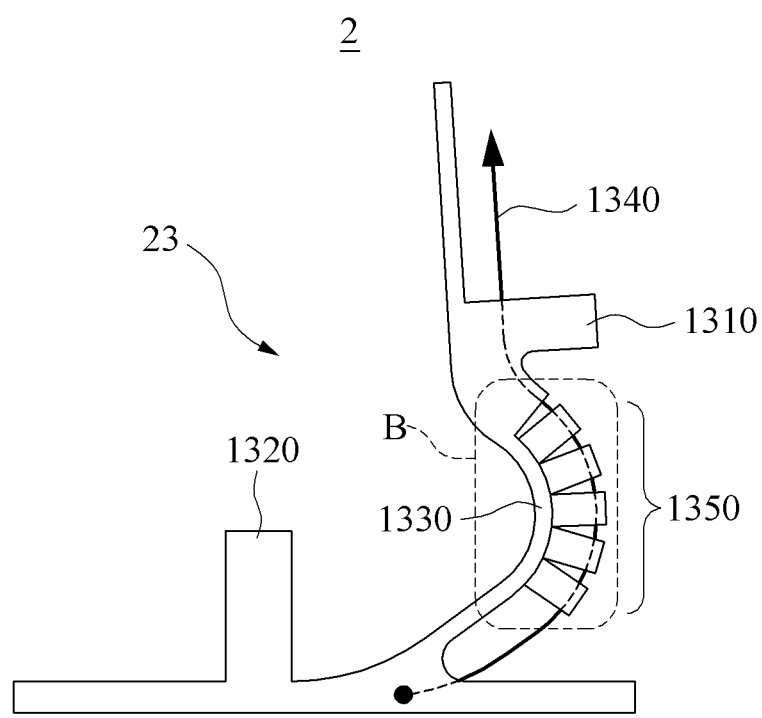
FIG. 31 illustrates a shape of a frame assembly when an ankle joint of a user is in a neutral state according to at least one example embodiment.
Figure 32:
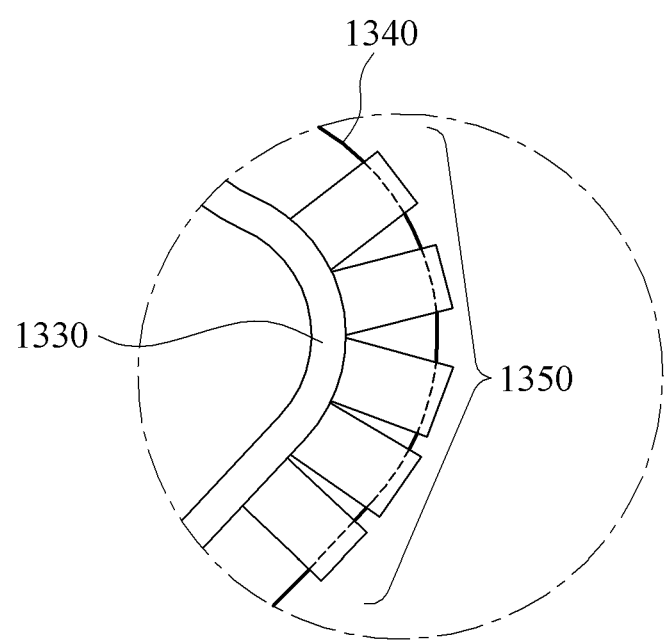
FIG. 32 illustrates a shape of a frame assembly when an ankle joint of a user is in an eversion motion state according to at least one example embodiment.

FIG. 31 illustrates a shape of a frame assembly when an ankle joint of a user is in a neutral state according to at least one example embodiment, and FIG. 32 illustrates a shape of the frame assembly when the ankle joint of the user is in an eversion motion state according to at least one example embodiment. FIG. 32 is an enlarged view of a shape of a portion B of FIG. 31.

For better understanding, descriptions will be provided based on a case in which angles between all the distance maintaining members 1350 of the frame assembly 23 are equal while an ankle joint is in a neutral state as shown in FIG. 31.

When the ankle joint performs an eversion motion, a lateral center of rotation of an ankle may move upward as shown in FIG. 29. Conversely, a medial center of rotation of the ankle may move downward. In this example, among a plurality of distance maintaining members 1350 positioned lateral to the ankle joint, a gap between distance maintaining members 1350 positioned on a relatively upper side may increase further than a gap between distance maintaining members 1350 positioned on a relatively lower side, whereby the frame assembly 23 may be self-aligned to cope with a change in the lateral center of rotation of the ankle. In detail, among the plurality of distance maintaining members 1350, a gap between distance maintaining members 1350 positioned relatively close to the center of rotation may increase further than a gap between distance maintaining members 1350 positioned relatively distant from the center of rotation, whereby the center of rotation of the frame assembly 23 may change. Thus, a user wearability may improve and an unnecessary load to be applied to the user may be reduced (or, alternatively, prevented).

The frame assembly 23 may be provided in a structure having symmetry on both sides from the ankle joint, similar to the frame assembly 22 of FIG. 22. Distance maintaining members respectively provided on both sides may be self-aligned separately. Thus, an issue of misalignment caused by the eversion/inversion motions as shown in FIGS. 19 and 20 may be solved.

The frame assembly 23 may have a flexibility and a multi-degree of freedom through the flexible first longitudinal member 1330, the second longitudinal member 1340, and the plurality of distance maintaining members 1350, and thus may solve the issue of misalignment.

In some example embodiments, the motion assistance apparatus 1, 2 may include a at least one sensor (not shown) and a controller (not shown).

The sensor may be a pressure sensor, a strain sensor or any other sensor configured to sense movement of the user and/or an angle of a joint of the user.

The controller may include a processor and a memory. The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The processor may processor may be an arithmetic logic unit, a digital signal processor, a microcomputer, a field programmable array, a programmable logic unit, a microprocessor or any other device capable of responding to and executing instructions in a defined manner. The memory may contain computer readable code that, when executed by the processor, configures the processor as a special purpose computer.

For example, the memory may contain computer readable code that, when executed by the processor, configures the processor as a special purpose computer to determine if the user is performing a flexion motion to, for example, sit down or an extension motion to, for example, stand up, based on information from the sensor. Further, the processor may control the actuator M to rotate the actuator M in different directions based on the determination. For example, in some example embodiments, the controller may instruct the actuator M to rotate in a counter-clockwise direction when the user is sitting down, and instruct the actuator M to rotate M in a clockwise direction when the user is standing up.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A frame assembly comprising:
a first longitudinal member;
A second longitudinal member spaced apart from the first longitudinal member; and
a plurality of distance maintaining members each having a first end and a second end, the first end connected to the first longitudinal member and the second end connected to the second longitudinal member, the plurality of distance maintaining members configured to maintain a distance between the first longitudinal member and the second longitudinal member, wherein
the first end of at least one of the plurality of distance maintaining members is fixed to the first longitudinal member and the second end of the at least one of the plurality of distance maintaining members is slidably connected to the second longitudinal member,
the second longitudinal member is configured to bend the frame assembly in a first direction, when a tensile force is applied to the second longitudinal member,
the second longitudinal member is configured to bend the frame assembly in a second direction opposite to the first direction, when a compressive force is applied to the second longitudinal member, the first end of the at least one of the plurality of distance maintaining members has a first height in a length direction of the first longitudinal member, the second end of the at least one of the plurality of distance maintaining members has a second height in a length direction of the second longitudinal member, and the first height is greater than the second height.

2. The frame assembly of claim 1, wherein the first longitudinal member and the second longitudinal member each have ends with an intermediate portion therebetween, and the plurality of distance maintaining members connect the first longitudinal member and the second longitudinal member such that the intermediate portion of the second longitudinal member moves relative to the intermediate portion of the first longitudinal member.

3. The frame assembly of claim 1, wherein the second longitudinal member is parallel with the first longitudinal member.

4. The frame assembly of claim 1, wherein
the frame assembly has ends with an intermediate portion therebetween, and
the intermediate portion of the frame assembly is configured to flex in response to a force applied in a lateral direction thereto.

5. The frame assembly of claim 1, wherein the first longitudinal member and the second longitudinal member each include a flexible material.

6. The frame assembly of claim 1, wherein a length of each of the plurality of distance maintaining members is less than a length of each of the first longitudinal member and the second longitudinal member.

7. The frame assembly of claim 1, wherein adjacent ones of the plurality of distance maintaining members are separated by a distance, the distance being less than a length of each of the plurality of distance maintaining members.

8. The frame assembly of claim 1, wherein at least one of the plurality of distance maintaining members has an intermediate portion between the first end and the second end.

9. The frame assembly of claim 8, wherein at least one of the first end and the second end of the at least one of the plurality of distance maintaining members is rotatably fixed to one of the first longitudinal member and the second longitudinal member.

10. The frame assembly of claim 1, wherein at least one of the plurality of distance maintaining members is slidably connected to one of the first longitudinal member and the second longitudinal member.

11. The frame assembly of claim 10, wherein the second longitudinal member has an intermediate portion between the first end and the second end, and the frame assembly further comprises:

a first object and a second object, wherein
the second end of the second longitudinal member is connected to the second object such that the second end of the second longitudinal member moves in a direction that intersects a longitudinal direction of the second object.

12. The frame assembly of claim 11, wherein the first object is configured to support a first portion of a user, and the second object is configured to support a second portion of the user, the first portion and the second portion of the user being on opposite sides of a joint of the user.

13. The frame assembly of claim 12, wherein, the frame assembly is configured to apply a torque to the second object to rotate the second object relative to the first object, if the tensile force is applied to the second longitudinal member.

14. The frame assembly of claim 11, wherein the first longitudinal member is an elastic body.

15. The frame assembly of claim 1, wherein the first longitudinal member and the second longitudinal member each have an intermediate portion between the first end and the second end, and the frame assembly further comprises:

a first object and a second object, the first object connected to the first end of the first longitudinal member and the first end of the second longitudinal member, and the second object connected to the second end of the first longitudinal member and the second end of the second longitudinal member.

16. A motion assistance apparatus comprising:
a first object configured to attach to a first portion of a user;
a second object configured to attach to a second portion of the user; and
a frame assembly including,
a first longitudinal member configured to connect the first object and the second object,
a second longitudinal member spaced apart from the first longitudinal member, and
a plurality of distance maintaining members each having a first end and a second end, the first end connected to the first longitudinal member and the second end connected to the second longitudinal member, wherein
the first end of at least one of the plurality of distance maintaining members is fixed to the first longitudinal member and the second end of the at least one of the plurality of distance maintaining members is slidably connected to the second longitudinal member,
the second longitudinal member is configured to bend the frame assembly in a first direction, when a tensile force is applied to the second longitudinal member,
the second longitudinal member is configured to bend the frame assembly in a second direction opposite to the first direction, when a compressive force is applied to the second longitudinal member,
the first end of the at least one of the plurality of distance maintaining members has a first height in a length direction of the first longitudinal member,
the second end of the at least one of the plurality of distance maintaining members has a second height in a length direction of the second longitudinal member, and
the first height is greater than the second height.

17. The motion assistance apparatus of claim 16, further comprising:
a rotary body connected to one of the first longitudinal member and the second longitudinal member,
wherein the frame assembly is configured to perform one of a flexion motion and an extension motion based on a direction of rotation of the rotary body.

18. The motion assistance apparatus of claim 16, wherein one of the first longitudinal member and the second longitudinal member is an elastic body, and
an initial state of the frame assembly is a flexion state.

* * * * *